United States Patent [19]
Tan et al.

[11] Patent Number: 5,648,561
[45] Date of Patent: Jul. 15, 1997

[54] PROCESS FOR THE PRODUCTION OF HIGH PURITY AND ULTRAPURE BISPHENOL-A

[75] Inventors: Qiu Tan; Minhua Zhang; Shenbo Yu; Zongzhang Liu; Shenghua Qian; Chuanzhao Li, all of Tianjin, China

[73] Assignees: China Petro-Chemical Corporation, Beijing; Tianjin University, Tianjin, both of China

[21] Appl. No.: 505,309

[22] PCT Filed: Feb. 16, 1994

[86] PCT No.: PCT/CN94/00011

§ 371 Date: Oct. 11, 1995

§ 102(e) Date: Oct. 11, 1995

[87] PCT Pub. No.: WO94/19302

PCT Pub. Date: Sep. 1, 1994

[30] Foreign Application Priority Data

Feb. 17, 1993 [CN] China ............... 93101417.4

[51] Int. Cl.⁶ .................. C07C 37/68; C07C 39/12
[52] U.S. Cl. ........................... 568/727; 568/724
[58] Field of Search ........................ 568/724, 727

[56] References Cited

U.S. PATENT DOCUMENTS

| | | | |
|---|---|---|---|
| 3,760,006 | 9/1973 | Gammill et al. ............ | 260/619 A |
| 3,849,076 | 11/1974 | Gryaznov et al. ........... | 23/288 R |
| 3,853,929 | 12/1974 | Cornelius et al. ........... | 260/407 |
| 4,045,379 | 8/1977 | Kwantes et al. ............. | 260/2.2 R |
| 4,096,616 | 6/1978 | Coffinberry ................ | 29/157.3 A |
| 4,124,069 | 11/1978 | Becker ..................... | 165/164 |
| 4,191,843 | 3/1980 | Kwantes et al. . | |
| 4,343,354 | 8/1982 | Weber ...................... | 165/165 |
| 4,351,966 | 9/1982 | Flock ....................... | 568/753 |
| 4,400,555 | 8/1983 | Mendiratta ................. | 568/728 |
| 4,590,303 | 5/1986 | Mendiratta ................. | 568/728 |
| 4,595,704 | 6/1986 | Fazio ....................... | 521/31 |
| 4,624,748 | 11/1986 | Haunschild ................. | 203/29 |
| 4,719,968 | 1/1988 | Speros ..................... | 165/154 |
| 4,740,634 | 4/1988 | Gomes de Matos et al. ..... | 568/724 |
| 4,766,254 | 8/1988 | Faler et al. ............... | 568/724 |
| 4,798,654 | 1/1989 | Limuro et al. .............. | 203/94 |
| 4,820,740 | 4/1989 | Li .......................... | 521/32 |
| 4,840,228 | 6/1989 | Shaner ..................... | 165/165 |
| 4,847,433 | 7/1989 | Kissinger .................. | 568/727 |
| 4,877,087 | 10/1989 | Hill ........................ | 165/181 |
| 4,918,245 | 4/1990 | Limuro et al. . | |
| 4,919,245 | 4/1990 | Braden ..................... | 165/10 |
| 4,937,051 | 6/1990 | Graven et al. .............. | 422/194 |
| 4,942,265 | 7/1990 | Limuro et al. .............. | 568/724 |
| 4,950,806 | 8/1990 | Limuro et al. .............. | 568/724 |
| 4,954,661 | 9/1990 | Limuro et al. .............. | 568/727 |
| 4,971,139 | 11/1990 | Khattar .................... | 165/86 |
| 5,075,511 | 12/1991 | Li .......................... | 568/727 |
| 5,087,767 | 2/1992 | Okamoto et al. . | |
| 5,105,026 | 4/1992 | Powell et al. .............. | 568/727 |
| 5,130,102 | 7/1992 | Jones, Jr. .................. | 422/191 |
| 5,133,942 | 7/1992 | Jones ...................... | 422/142 |
| 5,146,007 | 9/1992 | Cipullo . | |
| 5,158,754 | 10/1992 | Lefers et al. .............. | 422/191 |
| 5,184,675 | 2/1993 | Gardner .................... | 165/184 |
| 5,198,591 | 3/1993 | Kiedik et al. .............. | 568/727 |
| 5,210,329 | 5/1993 | Gomes de Matos et al. ..... | 568/727 |
| 5,269,887 | 12/1993 | Jakob et al. ............... | 568/724 X |
| 5,382,711 | 1/1995 | Asoaka et al. .............. | 568/724 X |
| 5,399,784 | 3/1995 | Asoaka et al. .............. | 568/724 X |
| 5,512,700 | 4/1996 | Patrascu et al. ............ | 568/724 |
| 5,527,971 | 6/1996 | McKinnie .................. | 568/724 X |

FOREIGN PATENT DOCUMENTS

| | | |
|---|---|---|
| 73 89 62 | 9/1969 | Belgium . |
| 0 332 203 B1 | 5/1993 | European Pat. Off. . |
| 3-284641 | 12/1991 | Japan . |

OTHER PUBLICATIONS

Japanese abstract: 01-238550, Sep. 22, 1989.
Japanese abstract; 62-192331, Aug. 22, 1987.

*Primary Examiner*—Paul F. Shaver
*Attorney, Agent, or Firm*—Chilton, Alix & Van Kirk

[57] ABSTRACT

High purity and ultrapure bisphenol A is prepared in a novel process.

25 Claims, 2 Drawing Sheets

PROCESS FOR THE PRODUCTION OF HIGH PURITY AND ULTRAPURE BISPHENOL-A

This application is a 371 of PCT/CN94/00011, filed Feb. 14, 1994.

TECHNICAL FIELD OF THE INVENTION

The present invention relates to a process for the production of high purity or polycarbonate grade and ultrapure bisphenol-A. More particularly, the present invention relates to a simplified process for the production of high purity and ultrapure 2,2-bis (4-hydroxyphenyl)propane (bisphenol-A, hereinafter sometimes referred to as "4,4-BPA" or "p,p-BPA" or simply identified as "BPA") in a high conversion of feedstocks(phenol and acetone) and a high selectivity to bisphenol-A by the condensation reaction of phenol and acetone in the presence of a modified ion-exchange resin catalyst using a novel multiple stage suspended reactive stripping technique and thereafter, without any intermediate concentration of the condensate or liquid condensation reaction mixture discharged from the reaction stage, by making use of a novel fine crystal destruction technique in the step of crystallization and a novel vapor-solid dephenolization technique in the step of phenol removal. In a further aspect, the present invention pertains to a novel arrangement of a multiple stage suspended reactive stripping apparatus from which the effluent is directly subjected to the step of crystallization operation without any intermediate concentration of the resulting condensation reaction mixture effluent since it has a bisphenol-A concentration sufficient to form immediately adduct crystals of bisphenol-A and phenol with 1:1 molar ratio when cooled.

BACKGROUND ART OF THE INVENTION

Bisphenol-A is a feedstock or intermediate product for the commercial production of various polymers including the polyarylates, polyamides, polyetherimides, polysulfones and polycarbonates, epoxy resins and modified phenol-formaldehyde resins. Colorless and high purity bisphenol-A has to be used to produce high quality polycarbonates.

Polycarbonates are in turn essential engineering plastics. They have excellent resistance to high temperatures, high impact resistance and good insulation resistance. These polymers play a more and more important role in the industrial fields such as, for example, chemical, mechanical and electric/electronic engineerings. Recently, laser data storage discs have found widespread applications in the industries such as, for example, computer and video-audio industries since optical data storage techniques have a variety of tremendous advantages. The feedstock for the production of an optical data storage substrate must be a polycarbonate which is prepared by means of nearly colorless and ultrapure bisphenol-A (the content of bisphenol-A is higher than about 99.99% by weight). An ultrapure bisphenol-A not only has higher purity but also should satisfy the extremely strict standards with respect to color, transmisivity, ash and iron contents or the like. This raises higher requirements in relation to the synthesis and purification of bisphenol-A than the production of usual polycarbonate grade bisphenol-A.

Bisphenol-A is produced by the condensation reaction of phenol and acetone, using an excess of phenol, in the presence of an acidic catalyst optionally with a promotor.

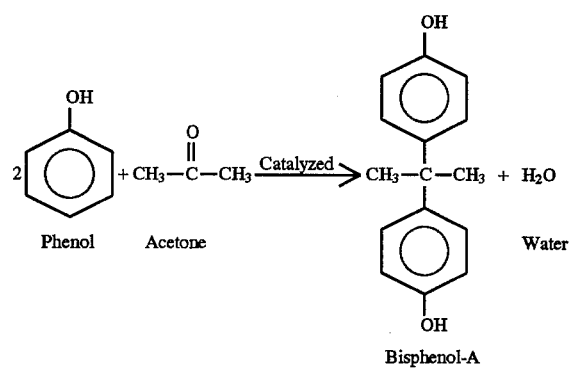

The reaction product mixture contains unreacted phenol and acetone, water formed during the reaction and by-products in addition to bisphenol-A.

The by-products which are formed during the condensation reaction of phenol and acetone include predominantly 2-(2-hydroxyphenyl)-2-(4-hydroxyphenyl)propane (hereinafter sometimes also simply identified as "2,4-BPA" or "o,p-BPA") and the Dianin's compound. Additionally, there are present in the reaction mixture small amounts of 2,4-bis [2-(4-hydroxyphenyl)isopropyl]phenol (hereinafter also sometimes identified as "triphenol"), polyphenol and some undesirable coloring substance. The presence of such by-products and impurities in a bisphenol-A product results in a decrease in the quality or performance properties of for example resins that are manufactured by making use of bisphenol-A.

In general, a process for the production of bisphenol-A comprises two essential stages, namely synthesis of bisphenol-A by means of the condensation reaction of phenol and acetone and subsequent purification of the resulting reaction mixture containing bisphenol-A.

The methods conventionally used in the synthesis of bisphenol-A include predominantly a "hydrochloric acid catalyzed method" and an "ion-exchange resin catalyzed method".

In the hydrochloric acid catalyzed method, hydrochloric acid as a catalyst is highly active and used in a small amount. The rate of the hydrochloric acid catalyzed reaction and the conversion of the starting materials, in particular acetone are high. However, the hydrochloric acid catalyzed method suffers from the disadvantages such as, for example, the strong corrosion of the acidic reaction solution on the apparatus used for the performance of the condensation reaction of phenol and acetone. Therefore, this process requires that the equipment for carrying out the condensation reaction and the subsequent treatments be made from particular types of materials. Additionally, the low selectivity of the reaction to the desired product and the decomposition of the obtained bisphenol-A are attributed to the presence of acidic substance during the distillation. Furthermore, a complicated purification installation is required for recovery of hydrochloric acid subsequent to the reaction and for purification of the obtained reaction product.

Moreover, the desired BPA product is susceptible to contamination. More importantly, all the equipment that is brought in contact with acidic substance must be made from special corrosion-resistant materials.

In some instances, sulfuric acid, sulfur compounds or other substances are employed as a cocatalyst or a promotor to improve the hydrochloric acid catalyzed method in some aspects but this has not overcome the disadvantages of the method for the production of bisphenol-A using an acid as a catalyst in general.

Alternatively, the ion-exchange resin catalyzed method employs a non-corrosive reaction system. Therefore, this method allows a variety of materials to be used for the manufacture of the reaction and successive treatment equipment and reduces in turn the expenditure of capital on the equipment to a great extent. Moreover, since an ion-exchange resin usable as a catalyst is generally insoluble in the reaction mixture system, it is easily separated after the condensation reaction and a quality bisphenol-A product can be thus obtained. In recent years, the conversion of the starting materials and selectivity to the desired bisphenol-A product have been improved to an important extent as the catalyst technology that is intimately associated with the ion-exchange resin catalyzed method advances continuously. As a result, this method is more and more extensively used in the synthesis of bisphenol-A. A great number of patents, patent applications and other publications have described the ion-exchange resin catalyzed method and in particular some of operation steps, specific resins and equipment used therein. For example, U.S. Pat. Nos. 3,073,868, 3,153,001, 3,172,916, 3,234,221, 3,873,275, 3,936,507, 4,054,611, 4,156,089, 4,209,646, 4,212,997, 4,215,011, 4,294,994, 4,308,404, 4,346,247, 4,354,046, 4,391,997, 4,400,555, 4,445,409, 4,471,154, 4,487,430, 4,492,807, 4,590,303, 4,740,634, 4,798,654, 4,847,433, 4,918,245, 4,950,806, 4,954,661, 5,087,767[also JP No. 64-332, 802 (Kokai)], 5,105,026, and 5,124,265; GB 159,668, 1,183,564, 1,340,869 and 2,053,019; DE 2,733,537; EP 0,144,735A, 0,268,318A, 0,319,326A3[CN 1,034,361A and also JP No. 62-304,941(Kokai)], 0,324,080, 0,329,075, 0,330,146, 0,332,877, 0,343,349 and 0,442,122A; JP No. Sho 36-23, 335(Kokoku), 38-1,368(Kokoku), 40-7,186(Kokoku), 47-43,937(Kokoku), 49-48,319 (Kokoku), 50-13,334 (Kokai), 54-159,378(Kokai), 55-27,1 08(Kokai), 56-46, 831 (Kokai), (Kokai), 57-88, 137 (Kokai), 60-122,004(Kokai), 61-78,741(Kokai), 62-148,441(Kokai), 62-178,532(Kokai), 63-56,335(Kokai) and 63-60,227(also CN 1,002,560C); SU 715,100 and CN 1,034,360A, 1,035,282A, 1,036,559A, 1,048,987A, 1,059,480A and 1,069,961 are concerned with the ion-exchange resin catalyzed methods more or less or some operation steps as well as the equipment and resin catalysts employed therein.

There have been proposed many processes for obtaining high purity bisphenol-A through the removal of the impurities or by-products which have formed during the condensation reaction.

In order to synthesize bisphenol-A in accordance with the ion-exchange resin catalyzed method, the following purification process is generally used: removing water, unreacted acetone and phenol from the liquid condensation reaction mixture by fractional distillation at a reduced pressure, then cooling the residual liquid mixture to precipitate bisphenol-A in the form of adduct crystals of bisphenol-A with phenol, further separating the resulting adduct crystals from the mixture containing by-products and impurities and finally removing phenol from the adduct crystals to obtain a high purity bisphenol-A product. Further, many processes are already provided for the treatment of the mother liquor from which the adduct crystals have been separated.

One of the methods for removing phenol from the adduct crystals of bisphenol-A and phenol is distillation method wherein phenol is distilled out at a reduced pressure. However, it is impossible to remove all the phenol present in the adduct crystals by making use of the distillation method. Therefore, it is necessary to perform a stripping step in a subsequent procedure as described in JP Nos. 47-43; 937(Kokoku) or 40-7, 186(Kokoku) or to conduct a recrystallization step with heated water as described in JP No. 57-88,137(Kokai).

More specifically, U.S. Pat. No. 3,049,569 to Francis N. Apel et al. describes a process for the production of ultrapure bisphenol-A comprising the steps of continuously contacting a mixture of acetone and excess of phenol with a substantially insoluble cationic exchange resin catalyst, separating the effluent from the reaction zone into two streams, isolating the reaction by-products and bisphenol-A from the first stream, dehydrating the second stream and recycling the reaction by-products, acetone and phenol which have been isolated to the reaction zone. According to Apel, a conversion of about 50% by weight is the most desirable since it provides yields of about 99% of the theoretical yield of bisphenol-A. The resulting reaction mixture contains only about 15% by weight of bisphenol-A. Therefore, the mixture must be concentrated and the recycle quantities are extremely large. Moreover, the purity in the order of about 99% is obtained (about 99.7% is obtained in the example).

U.S. Pat. No. 3,873,275 to Richard C. Bennett describes in general a crystallization apparatus and method wherein the mother liquor recirculation rate and the size of crystal particles removed through a fine crystal destruction circuit are independently regulated so that undesirable fine crystals removed from the slurry body undergoing crystallization and the residence time thereof are regulated to provide a product of substantially improved size uniformity. However, the Bennett apparatus is considerably complicated and the performance of the apparatus is difficult to be adjusted or controlled.

U.S. Pat. No. 4,209,646 to Caluire R. Gac et al. describes a process for purifying diphenylol propane (bisphenol-A) by preparing a liquid of from about 10% to about 50% by weight diphenylol propane, phenol and less than about 15% by weight of water at a temperature of from about 70° C. to about 100° C. and applying a reduced pressure such as from about 20 to about 120 mmHg thereto which corresponds to the vapor pressure of the mixture while simultaneously cooling the same to precipitate almost pure diphenylolpropane in the form of crystals. However, the obtained diphenylolpropane still contains up to about 2% by weight of impurities and the coloration of the diphenylolpropane crystals corresponds to 30APHA after melting.

U.S. Pat. No. 4,215,011 to Lawrence A. Smith, Jr. discloses a catalyst system for use in a reaction-distillation column comprising a plurality of closed cloth pockets containing a particulate catalytic material arranged and supported in said reaction-distillation column by a wire mesh that is intimately associated with said closed cloth pockets. This complicated arrangement of catalytic particles is particularly provided for use in the separation of isoolefins from streams containing mixtures of at least one isoolefin and the corresponding normal olefin. This patent is especially useful for the separation of isobutene from a stream containing normal butenes. It is not known to be useful or to have ever been used in the preparation of bisphenol-A.

U.S. Pat. No. 4,294,994 to Ming K. Li describes a method for removal of phenol from the adduct of bisphenol-A and phenol by subjecting the adduct feed at a temperature of from about 50° to about 150° C. to spray drying conditions such as at a temperature of from about 150° to about 250° C. with a small amount of liquid carrier having a boiling point below that of phenol and recovering the bisphenol-A product from the released phenol. The purity of the obtained bisphenol-A product, as shown in example 2 provided by Li, is up to about 99% by weight though it is obviously disadvantageous that the adduct of bisphenol-A and phenol experiences high temperature effect of up to about 250° C. whereby degradation or undesirable reactions thereof usually occur.

U.S. Pat. No. 4,308,404 to Arien Kwantes et al. proposes an improved continuous process for preparing bisphenols such as bisphenol-A from phenol and acetone in the presence of an acidic ion-exchange resin catalyst in a reaction zone comprising a series of reactors wherein a part of the effluent from at least one reactor with the exception of the last reactor is recycled to the preceding reactor, preferably to the first reactor, and the ratio of the recycled stream to the stream fed to the following reactor (the recycle ratio) is in the range of from about 0.1:1 to about 10:1. Nevertheless, the Kwantes' manner of operation undoubtedly results in a substantial reduction in the reaction rate as the condensation reaction proceeds.

U.S. Pat. No. 4,351,966 to John W. Flock relates to a process for recovery of phenol from the tarry residue derived during the manufacture of bisphenol-A. According to Flock, the bisphenol tar is treated at temperatures of from about 200° to about 500° C. and atmospheric pressure to recover all of the trapped phenol and the phenol liberated from a variety of phenol-based compounds. Flock uses so-called molecular sieve catalyst, that is cryctalline hydrated silica-alumina catalyst.

U.S. Pat. No. 4,354,046 to Glem R. Ladewig et al. provides a process for improving the purity and yield of bisphenol-A by feeding the crude bisphenol-A containing any unreacted phenol and acetone as well as the water formed during the condensation reaction removed from the condensation reactor to a crystallizer, adding an organic solvent such as toluene and water, heating the resulting mixture to form a single liquid phase, cooling the liquid phase to obtain crystals of bisphenol-A, separating the solvent and water from the resulting mother liquor, mixing phenol with the mother liquor, contacting the mixture with a cation-exchange resin catalyst or hydrochloric acid to convert the impurities to bisphenol-A, removing phenol from the mixture and recycling the remainder and the separated phenol to the crystallizer and the condensation reactor, respectively. It can be obviously seen that the product yield of p,p-bisphenol and the conversion of the total impurities are about 95%, respectively.

U.S. Pat. No. 4,391,997 to Ashok K. Mendiratta describes a process for the production of bisphenol-A comprising reacting phenol and acetone in the presence of a cation-exchange resin as a catalyst in a continuous reactor system in which the reaction temperatures increases along the length of the reactor or alternatively, the reaction takes place in a series of reactors operated at progressively increasing temperatures to produce a condensation reaction mixture of bisphenol-A, phenol, acetone, water and phenol/acetone condensation reaction by-products which may be then treated by any conventional means to form a bisphenol-A product having limited quantities of coloring substance and other condensation reaction by-products or impurities. It is attempted according to Mendiratta's teachings to reduce the amount of by-products or impurities and the material losses, thereby improving the material usage and the quality of BPA in the system employed. However, the conversion and selectivity of the acetone reaction is also remarkably limited. Actually, at a phenol to acetone molar ratio of about 10.7:1 and the temperature of about 90° C., the conversion of acetone remains constant at about 69%. Under steady operation conditions, p,p-bisphenol-A is formed in yields of about 94+ percent and p,p-BPA plus o, p-BPA are formed in combination in yields of from about 98+ to about 99+ percent (based on p,p-BPA, o, p-BPA and other minor by-products). The selectivity of p,p-BPA is believed to be possibly as great as only about 96% (based on p, p-BPA, o,p-BPA and other minor by-products).

U.S. Pat. No. 4,400,555 to Ashok K. Mendiratta provides an improved bisphenol-A synthesis reactor system using a multiple acetone injection technique in a cation-exchange resin catalyzed bisphenol-A production process. Ashok K. Mendiratta intends to yield high material usage and to improve bisphenol-A product color or hue as well as to reduce the equipment capital expenditure/operating costs involved with recovery and recycling of excess phenol for the same overall phenol to acetone ratio charged to the reactor system. In operation, 25–75% of the feedstream of acetone is injected to the first reactor or the beginning of the reactor and the remainder is injected to the subsequent reactors or along the length of the reactor and all of phenol is charged to the first reactor or the beginning of the reactor. It is believed that this procedure allows a high relative phenol concentration to be maintained during most of the condensation reaction process while the overall phenol to acetone molar ratio is reduced to be as low as possible. According to Mendiratta, the conversion and selectivity to p, p-BPA of acetone reaction are significantly limited [the yield of p, p-BPA is about 94+ percent and the yield of p,p-BPA and o,p-BPA in combination is only from about 98+ to about 99+ percent (based on p,p-BPA, o,p-BPA and other minor by-products)] by means of the multiple acetone injection system.

U.S. Pat. No. 4,471,154 to Frederick C. Franklin suggests a staged and fluidized bed distillation reactor including a reactor vessel containing a plurality of trays vertically spaced from one another and interconnected by means of respective downcomers for conducting reaction liquid downward from tray to tray, at least some of said trays further containing a quantity of a particulate catalyst which is confined within a containing volume by a screen in connection to each of the trays and fluidized by the action of vapor. When operation is started, a stream of vapor and a stream of liquid pass through the respective trays containing the catalyst thereon upward and downward, respectively. The lower and higher boiling materials are removed from the upper and lower portions of the distillation reactor, respectively. It is evident in view of teachings of Frederick C. Franklin that this patent is focused on conducting a reaction of reactants A and B by providing a staged and fluidized bed distillation reactor rather than on improving the purity and hue or color of a bisphenol-A product and at the same time simplifying the process for the production of bisphenol-A.

U.S. Pat. No. 4,492,807 to Viney P. Aneja suggests that up to about 15% by weight of water and up to about 15% by weight of an organic liquid be simultaneously added to a mixture comprising impure bisphenol-A and phenol. The organic liquid should not react with bisphenol-A or phenol and dissolves a substantial proportion of the impurities or by-products formed in the synthesis of bisphenol-A. Preferred organic liquids are toluene and acetone. The Aneja's invention is advantageous in that a pronounced increase in recovery of bisphenol-A such as up to about 90% recovery is obtained without a significant sacrifice in product purity. Obviously, the recovery and purity are not so improved as expected.

U.S. Pat. No. 4,590,303 to Ashok K. Mendiratta is concerned with a method for the preparation of bisphenol-A from phenol and acetone wherein from about 5% to about 70% by weight of acetone feed per hour based on the weight of total acetone feed charged to the condensation reactor per hour, preferably from about 10 to about 40% by weight is diverted and delivered to the rearrangement reactor so that the product distribution of the condensation reactor effluent is substantially maintained. It is reported that as a result of diversion of the total acetone feed to the rearrangement reactor, improved acetone conversion is realized and BPA productivity is enhanced. However, the highest overall acetone conversion is about 65% by weight, though there may be increase of about 35% in acetone conversion.

U.S. Pat. No. 4,740,634 to Isabel M. Gones de Matos et al. discloses a special aspect of the process for the preparation of bisphenol-A wherein water is added to the mixture comprising bisphenol-A, from about 0.5 to about 15 percent by weight of diphenol isomers and other impurities but essentially no phenol. The resulting mixture is brought to a temperature sufficient to melt the solid material present therein and then cooled to a temperature below about 90° C. to form bisphenol-A crystals which are thereafter separated, washed and dried to obtain a bisphenol-A product. However, thus obtained bisphenol-A product has an initial absorbance of 0.111 and contains only less than about 99.5 percent by weight of p, p-BPA even if it is further purified by contacting with an organic solvent.

U.S. Pat. No. 4,798,654 to Shigeru Iimuro et al. teaches a process for preparing bisphenol-A comprising distilling the intermediate adduct of bisphenol-A and phenol at a temperature in a range from about 160° C. to about 200° C. in a dephenolization column, recovering phenol from the top of the distillation column and bisphenol-A from the bottom of the distillation column and recycling a part of bottom liquid to the adduct feed of bisphenol-A and phenol. It is said in the Iimuro disclosure that plugging of the distillation column is prevented and continuous operation for a long period of time such as one year is possible. However, the phenol content of the bisphenol-A product taken out of the bottom of the dephenolization column is still up to about 2%.

U.S. Pat. No. 4,847,433 Gaylord M. Kissinger provides a process for preparing dihydric phenols such as bisphenol-A which process is based on the finding that there are significant quantities of acidic impurities derived from the acidic ion-exchange resin catalyst in the stream which is recovered from the catalyst. These impurities are believed to cause the bisphenol-A product to disappear (breakdown). Therefore, Kissinger suggests that acid neutralizing effective amounts of a carbonate of a Group II—a metal or transition metal of oxidation number +2 be added with barium carbonate being particularly preferred. Data as to the purity of in particular bisphenol-A and the conversion of acetone are not found in the Kissinger's disclosure.

U.S. Pat. No. 4,918,245 to Shigeru Iimuro et al. describes a process for the preparation of bisphenol-A. According to '245, (1) one mole of acetone is reacted with 4 to 12 moles of phenol in the presence of a sulfonic acid type cation exchange resin catalyst modified with a mercapto group—containing compound such as mercaptoethylamine to convert from about 20 to about 60% of acetone, and (2) the reaction mixture containing unreacted acetone is successively reacted in the presence of the hydrochloric acid catalyst. However, the drawback of '245 is that the hydrochloric acid catalyst is used and even so the purity of the p,p-BPA thus obtained is only about 98.3% as shown in only one example of this invention.

U.S. Pat. No. 4,950,806 Shigeru Iimuro et al. describes a process for crystallizing an adduct of bisphenol-A with phenol from a phenol solution of bisphenol-A in the presence of water, said process comprising the steps of controlling the concentration of bisphenol-A in said solution by removing a portion of the phenol from said solution or adding phenol to said solution according to feedback control based on the measurement of solution density to obtain an adjusted solution containing from 20 to 50% by weight of bisphenol-A, and feeding the adjusted solution to the crystallizer to form a solution having a temperature of from about 35° C. to about 70° C. and maintaining the inside wall of the crystallizer at a temperature higher than that of the solution, provided the temperature difference is smaller than 5° C. This patent is also disadvantageous in that hydrogen chloride is used as a catalyst and the reaction mixture issued from the reaction system must be concentrated.

U.S. Pat. No. 4,954,661 to Shigeru Iimuro et al. discloses a method for preparing high purity or high quality bisphenol-A by recovering in a high yield bisphenol-A from the mother liquor from which the adduct of bisphenol-A with phenol has been separated and removing coloring substances and other impruities. According to the first aspect of Iimuro's invention, a portion of the by-products which are not recovered as bisphenol-A are withdrawn from the reaction system with the same being prevented from recycling to any process or recycling the same to each process is minimized and therefore the bisphenol-A can not contaminated with such by-products due to the accumulation thereof. Furthermore, sinceall the withdrawn portions of the by-products which can be recovered to obtain bisphenol-A may be returned to the principal reaction process, it is possible to increase the productivity of each process to the maximum extent. This patent only teaches an overall process which involves operations such as concentration, crystallization and cleavage or cracking, etc. subsequent to the condensation reaction of phenol and acetone.

U.S. Pat. No. 5,087,767 to Kenichi Okamoto et al. suggests a method for preparing 2,2-bis(4-hydroxyphenyl) propane comprising reacting acetone and phenol in the presence of an acidic ion-exchange resin as a catalyst wherein the reaction of acetone and phenol is performed while removing a part of the water generated during the reaction from a mixed solution containing acetone and phenol by a pervaporation method with a selectively water-permeable membrane such as porous glass, silica, alumina and ceramic membranes. According to the method described in this patent, the water generated through the reaction can rapidly be removed simultaneously with or alternatively to the reaction by a pervaporation operation and, therefore, the catalytic activity of the ion-exchange resin is not impaired at all. Moreover, any complicated operations associated with dehydration are not required. Thus, the acidic ion-exchange resin catalyst can continuously be used over a long time period without any treatment for the regeneration thereof. Further, according to the method of this patent, bisphenol-A can be economically prepared from acetone and phenol in a high conversion rate and good yield. However, as shown in the illustrative examples, the capacity of removing water is not strong so that after about 8 hours of the condensation reaction in a batch stirred reactor the conversion of acetone or the yield of p, p-bisphenol-A amounts to about 75% for an inorganic-organic composite membrane, about 80% for an organic membrane and about 90% for an inorganic membrane.

U.S. Pat. No. 5,105,026 to Joseph B. Powell is concerned with improvements to the purity of a bisphenol product in a bisphenol by-product isomerization process wherein isomers of bisphenol are isomerized to the desired bisphenol product. During the isomerization, acidic resin fines elute from the acidic ion-exchange resin isomerization catalyst into the reaction effluent. These resin fines can be filtered effectively and without contamination by a bed of solid particles such as alumina or carbon. The removal of resin fines improves the product quality and yield by eliminating resin particulates and reducing acid catalyzed cracking of bisphenols during successive purification and finishing steps.

U.S. Pat. No. 5,133,942 Edward M. Jones provides an arrangement for concurrently carrying out chemical reactions in a distillation column reactor, separating by fractional distillation the reactants and reaction products, removing the reaction catalyst from a distillation column reactor and replacing the used catalyst with fresh and/or regenerated catalyst. The distillation column contains a plurality of suitable liquid-vapor contact trays. Each of said trays have a downcomer and weir associated therewith, said downcomer connecting each said tray to the tray below each said tray. A solid particulate catalyst is supported on at least a portion of said trays by wire mesh or screen or filter medium and submerged to approximately the depth of the liquid on said trays. The vapor rising through the liquid on the trays tends to keep the particulate catalyst in the form of suspension in the liquid. Obviously, there are a lot of chemical reactions which can not be carried out because the reaction temperature of the reactants and the distillation temperature of the component or product to be separated out by fractional distillation are not consistent with each other or there is a great difference therebetween.

EP 0,319,326A3 to Shigeru Iimuro et al. provides a process for preparing 2,2-bis (4-hydroxyphenyl) propane (also bisphenol-A) of high purity. Actually, Shigeru Iimuro et al. simply suggests a pretreatment step before the adduct of bisphenol-A with phenol, in particular that obtained by the condensation reaction of acetone and phenol and subsequent treatments such as, for example distillation or concentration and crystallizations of the resulting reaction mixture is subjected to the dephenolization operation. According to the Iimuro's invention, the adduct is washed with phenol which itself is obtained as a by-product when the adduct of bisphenol-A and phenol is decomposed to give a bisphenol-A product. It is reported in the Iimuro's description that the hue of bisphenol-A obtained by the decomposition of the washed adduct is about 10 APHA and the purity of the bisphenol-A product was believed to be satisfactory as a material for use in the manufacture of an optical storage polycarbonate. However, the purity of the bisphenol-A product is not specifically given in the Iimuro's disclosure.

JP No. 61-78,741 assigned to Mitsui Toatsu Chemicals, Inc. describes a process for the production of 2,2-bis (4-hydroxyphenyl) propane (BPA) wherein the mixed reaction solution containing phenol and acetone is brought into contact simultaneously or alternatively with an ion-exchange resin and a dehydrating agent. The provided examples as a consequence, reports that after about 8 hours of the condensation reaction in such a manner the conversion is at most about 95% and the purity of the obtained bisphenol-A product does not exceed about 97.5%.

CN 1,069,961A is directed to the preparation and purification of the adduct crystals of bisphenol-A and phenol, crystallization means and process for the preparation of a high quality bisphenol-A product. According to the teachings of this patent application, the reaction mixture issued from the condensation reaction of acetone and excess phenol is passed through a plurality of crystallization treatment stages and the adduct of bisphenol-A and phenol which is meanwhile crystallized and separated in the respective crystallization stages is brought into intimate contact with a phenol product which is already purified in accordance with a specific manner to wash and purify the adduct crystals thoroughly. Thereafter, phenol is removed from the adduct crystals by means of for example evaporation, extraction and steam stripping. It is asserted in the disclosure of this application that bisphenol-A having a high purity, a good hue (less than 15 APHA), good storage stability and resistance to coloration when it is melted may be obtained. Obviously, there is only stressed in the application the performance of the crystallization operation of the already formed adduct crystals of bisphenol-A and phenol rather than how to increase the purity of the obtained bisphenol-A through the improvements to various operation steps with a simplified reactor system and subsequent treatment means.

Although the bisphenol-A product obtained after the purification operations in accordance with the ion-exchange resin catalyzed method may meet the requirements as to the quality of bisphenol-A usable for the manufacture of conventional polycarbonates, there is heretofore unknown an ultrapure bisphenol-A product having a purity of such as, for example, more than about 99.95% or even about 99.99% sufficient for use in the manufacture of for example optical data storage materials.

Since the processes for the synthesis of higher purity bisphenol-A according to the ion-exchange resin catalyzed methods so far proposed in the literature such as in the above-mentioned patents and patent applications use higher molar ratios of phenol to acetone which is in general higher than about 8:1 and at the same time there are some limitations to the reaction temperature and residence time, etc., the concentration of bisphenol-A in the resulting liquid condensation reaction mixture is very low, typically below about 15%. Therefore, the liquid condensation reaction mixture must be concentrated before it is cooled to precipitate adduct of bisphenol-A and phenol in the form of crystals. Heretofore, there has been no proposal for omitting the concentration step since direct crystallization of the highly dilute condensation reaction solution undoubtedly results in very low yield of bisphenol-A and fully unacceptable color or hue of more than 15 APHA, thereby reducing the purity of thus obtained bisphenol-A product significantly. To concentrate the reaction mixture means that the process stream is subjected to strong thermal effect once more, thereby leading possibly to the decomposition or secondary reactions of the desired reaction product to form coloring substance because the liquid condensation reaction mixture from the reactor system contains slightly acidic impurities.

Moreover, the ion-exchange resin catalyzed methods as described in for example the above-mentioned patents or patent applications are still disadvantageous in that the condensation reaction rate is low and the residence time of feedstocks is long in the reactor system. The after treatment is complicated and highly loaded due to the high ratio of phenol to acetone and large amount of recycle unreacted phenol stream. In some instances, the reactor systems used are difficult to assemble or disassemble. For the bag construction as described in U.S. Pat. No. 4,487,430, some liquid may flow through the spaces between the bags.

Therefore, it is always desirable to further improve the conventional processes or some steps thereof in various aspects or further to develop novel processes for producing higher and higher quality (purity and coloration, etc.) bisphenol-A products to meet great demand in industrial applications although there have been a great number of processes for the production of bisphenol-A (BPA) which have shown separately some advantages over their respective preceding processes and have been described in a variety of patents and other publications such as those mentioned above.

DISCLOSURE OF THE INVENTION

It has now been found that bisphenol-A can be more simply and more economically produced in a process which comprises using a specially designed multiple stage suspended reactive stripping technique for the condensation reaction of phenol and acetone in the presence of a modified ion-exchange resin as a catalyst wherein an inert gaseous stream is employed as a stripping medium, in combination with novelly developed fine crystal destruction technique and/or vapor-solid dephenolization technique but without any intermediate concentration of the condensation reaction mixture which is discharged from the condensation reactor system before it is subjected to crystallization, thereby providing for production of not only a polycarbonate grade bisphenol-A product but also an ultrapure bisphenol-A product, and at the same time importantly reducing expenditure of capital on the equipment and operation costs.

Accordingly, one of objects of the present invention is to provide a process for the production of high purity bisphenol-A comprising reacting phenol and acetone in a multiple stage suspended reactive stripping apparatus to form a reaction mixture having a high bisphenol-A content.

Another object of the present invention is to provide a process for the production of high purity bisphenol-A comprising directly subjecting the reaction mixture containing bisphenol-A product from the reactive stripping apparatus t A further obnventiode a process for the production of high purity bisphenol-A comprising cooling the reaction mixture containing bisphenol-A product in a crystallizer having two filter means provided therein and connected with at least one crystal destructor.

A still further object of the present invention is to provide a process for the production of high purity bisphenol-A comprising removing phenol from adduct crystals of bisphenol-A and phenol in a gas-solid dephenolizer.

A still further object of the present invention is to provide a process for the production of ultrapure bisphenol-A comprising subjecting bisphenol-A crystals from a dephenolizer to recrystallization.

A still further object of the present invention is to provide a process for the production of high purity or ultrapure bisphenol-A in good yields and high selectivity comprising subjecting the mother liquor obtained after separation of adduct crystals of bisphenol-A and phenol to concentration, secondary crystallization and separation of crystals followed by recyling secondary crystals to the reaction mixture effluent discharged from the reactive stripping apparatus.

According to one of embodiments of the present invention, there is provided a process for the production of high purity bisphenol-A comprising (1) reacting from about 4 to about 12 times molar excess of phenol and acetone in the presence of a modified cation-exchange resin as a catalyst in a substantially vertical, multiple stage suspended reactive stripping apparatus comprising
   (i) a plurality of perforated trays provided therein,
   (ii) a first screen located on each tray,
   (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
   (iv) a solid particulate catalyst contained within the catalyst chamber, at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions, and to strip water from the reaction mixture (2) cooling the liquid condensation reaction mixture effluent from the reactive stripping apparatus in a crystallizer to form a slurry containing crystals of the adduct of bisphenol-A and phenol in 1:1 in 1:1 molar ratio and the mother liquor, (3) separating the adduct crystals from the mother liquor optionally followed by washing the separated adduct crystals, and (4) removing phenol from the adduct crystals obtained in step (3) above to obtain a high purity bisphenol-A product.

According to another embodiment of the present invention, there is provided a process for the production of high purity bisphenol-A comprising (1) reacting from about 4 to about 12 times molar excess of phenol and acetone in the presence of a modified cation-exchange resin as a catalyst in a substantially vertical, multiple stage suspended reactive stripping apparatus comprising
   (i) a plurality of perforated trays provided therein,
   (ii) a first screen located on each tray,
   (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
   (iv) a solid particulate catalyst contained within the catalyst chamber, at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions and to strip water from the reaction mixture, (2') cooling the liquid condensation reaction mixture effluent from the reactive stripping apparatus in a crystallizer to form a slurry containing crystals of the adduct of bisphenol-A and phenol in 1:1 molar ratio and the mother liquor, said crystallizer having two filter means provided therein whereby a portion of the slurry containing fine adduct crystals of bisphenol-A and phenol having a particle size less than that of predetermined crystal cut is allowed to pass alternatively through one of filter means with a circulating pump and is then introduced into at least one fine crystal destructor from which a solution obtained after destruction of fine crystals is returned to the crystallizer alternatively through the other filter means with said or another circulating pump, (3) separating the adduct crystals from the mother liquor optionally followed by washing the separated adduct crystals, and (4) removing phenol from the adduct crystals obtained in step (3) above to obtain a high purity bisphenol-A product.

According to a further embodiment of the present invention, there is provided a process for the production of high purity bisphenol-A comprising (1) reacting from about 4 to about 12 times molar excess of phenol and acetone in the presence of a modified cation-exchange resin as a catalyst in a substantially vertical, multiple stage suspended reactive stripping apparatus comprising (i) a plurality of perforated trays provided therein,
  (ii) a first screen located on each tray,
  (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
  (iv) a solid particulate catalyst contained within the catalyst chamber, at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions and to strip water from the reaction mixture, (2) cooling the liquid condensation reaction mixture effluent from the reactive stripping apparatus in a crystallizer to form a slurry containing crystals of the adduct of bisphenol-A and phenol in 1:1 molar ratio and the mother liquor, (3) separating the adduct crystals from the mother liquor optionally followed by washing the separated adduct crystals, and (4') removing phenol from the adduct crystals obtained in step (3) above by introducing the adduct crystals into a vacuum or inert gaseous flow dephenoizer, bringing the adduct crystals to a temperature below the melting point thereof in vacuum or in the presence of an inert gaseous stream to decompose the crystals into a gas phase and a solid phase, withdrawing the gas phase in vacuum or with the inert gaseous stream and discharging the solid phase as a high purity bisphenol-A product.

According to a still further embodiment of the present invention, there is provided a process for the production of high purity bisphenol-A comprising (1) reacting from about 4 to about 12 times molar excess of phenol and acetone in the presence of a modified cation-exchange resin as a catalyst in a substantially vertical, multiple stage suspended reactive stripping apparatus comprising (i) a plurality of perforated trays provided therein,
  (ii) a first screen located on each tray,
  (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
  (iv) a solid particulate catalyst contained within the catalyst chamber, at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions and to strip water from the reaction mixture, (2') cooling the liquid condensation reaction mixture effluent from the reactive stripping apparatus in a crystallizer to form a slurry containing crystals of the adduct of bisphenol-A and phenol in 1:1 molar ratio and the mother liquor, said crystallizer having two filter means provided therein whereby a portion of the slurry containing fine adduct crystals of bisphenol-A and phenol having a particle size less than that of predetermined crystal cut is allowed to pass alternatively through one of filter means with a circulating pump and is then introduced into at least one fine crystal destructor from which a solution obtained after destruction of fine crystals is returned to the crystallizer alternatively through the other filter means with said or another circulating pump, (3) separating the adduct crystals from the mother liquor optionally followed by washing the separated adduct crystals, and (4') removing phenol from the adduct crystals obtained in step (3) above by introducing the adduct crystals into a vacuum or inert gaseous flow dephenolizer, bringing the adduct crystals to a temperature below the melting point thereof in vacuum or in the presence of an inert gaseous stream to decompose the crystals into a gas phase and a solid phase, withdrawing the gas phase in vacuum or with the inert gaseous stream and discharging the solid phase as a high purity bisphenol-A product.

According to a still further embodiment of the present invention, there is provided a process for the production of ultrapure bisphenol-A comprising (1) reacting from about 4 to about 12 times molar excess of phenol and acetone in the presence of a modified cation-exchange resin as a catalyst in a substantially vertical, multiple stage suspended reactive stripping apparatus comprising (i) a plurality of perforated trays provided therein,
  (ii) a first screen located on each tray,
  (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
  (iv) a solid particulate catalyst contained within the catalyst chamber, at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions and to strip water from the reaction mixture, (2) cooling the liquid condensation reaction mixture effluent from the reactive stripping apparatus in a crystallizer to form a slurry containing crystals of the adduct of bisphenol-A and phenol in 1:1 molar ratio and the mother liquor, (3) separating the adduct crystals from the mother liquor optionally followed by washing the separated adduct crystals, (4) removing phenol from the adduct crystals obtained in step (3) above to obtain high purity bisphenol-A crystals, (5) recrystallizing the high purity bisphenol-A crystals obtained in step (4) above in the presence of solvent in a recrystallizer, and (6) separating the bisphenol-A crystals from the mother liquor optionally followed by washing the separated bisphenol-A crystals to obtain an ultrapure bisphenol-A product.

According to a still further embodiment of the present invention, there is provided a process for the production of ultrapure bisphenol-A comprising (1) reacting from about 4 to about 12 times molar excess of phenol and acetone in the presence of a modified cation-exchange resin as a catalyst in a substantially vertical, multiple stage suspended reactive stripping apparatus comprising
  (i) a plurality of perforated trays provided therein,
  (ii) a first screen located on each tray,
  (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
  (iv) a solid particulate catalyst contained within the catalyst chamber, at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions and to strip water from the reaction mixture, (2') cooling the liquid condensation reaction mixture effluent from the reactive stripping apparatus in a crystallizer to form a slurry containing crystals of the adduct of bisphenol-A and phenol in 1:1 molar ratio and the mother liquor, said crystallizer having two filter means provided therein whereby a portion of the slurry containing fine adduct crystals of bisphenol-A and phenol having a particle size less than that of predetermined crystalcut is allowed to pass alternatively through one of filter means with a circulating pump and is then introduced into at least one fine crystal destructor from which a solution obtained after destruction of fine crystals is returned to the crystallizer alternatively through the other filter means with said or another circulating pump, (3) separating the adduct crystals from the mother liquor optionally followed by washing the separated adduct crystals, (4) removing phenol from the adduct crystals obtained in step (3) above to obtain high purity bisphenol-A crystals, (5) recrystallizing the high purity bisphenol-A crystals obtained in step (4) above in the presence of solvent in a recrystallizer, and (6) separating the bisphenol-A crystals from the mother liquor optionally followed by washing the separated bisphenol-A crystals to obtain an ultrapure bisphenol-A product.

According to a still further embodiment of the present invention, there is provided a process for the production of ultrapure bisphenol-A comprising (1) reacting from about 4 to about 12 times molar excess of phenol and acetone in the presence of a modified cation-exchange resin as a catalyst in a substantially vertical, multiple stage suspended reactive stripping apparatus comprising
  (i) a plurality of perforated trays provided therein,
  (ii) a first screen located on each tray,
  (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
  (iv) a solid particulate catalyst contained within the catalyst chamber, at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions and to strip water from the reaction mixture (2) cooling the liquid condensation reaction mixture effluent from the reactive stripping apparatus in a crystallizer to form a slurry containing crystals of the adduct of bisphenol-A and phenol in 1:1 molar ratio and the mother liquor, (3) separating the adduct crystals from the mother liquor optionally followed by washing the separated adduct crystals, (4') removing phenol from the adduct crystals obtained in step (3) above by introducing the adduct crystals into a vacuum or inert gaseous flow dephenolizer, bringing the adduct crystals to a temperature below the melting point thereof in vacuum or in the presence of an inert gaseous stream to decompose the crystals into a gas phase and a solid phase, withdrawing the gas phase in vacuum or with the inert gaseous stream and discharging the solid phase as high purity bisphenol-A crystals, (5) recrystallizing the high purity bisphenol-A crystals obtained in step (4) above in the presence of solvent in a recrystallizer, and (6) separating the bisphenol-A crystals from the mother liquor optionally followed by washing the separated bisphenol-A crystals to obtain an ultrapure bisphenol-A product.

According to a still further embodiment of the present invent, there is provided a process for the production of ultrapure bisphenol-A comprising (1) reach from about 4 to about 12 times molar excess of phenol and acetone in the presence of a modified cation-exchange resin as a catalyst in a substantially vertical, multiple stage suspended reactive stripping apparatus comprising
 (i) a plurality of perforated trays provided therein,
 (ii) a first screen located on each tray,
 (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
 (iv) a solid particulate catalyst contained within the catalyst chamber,
at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions and to strip water from the reaction mixture,
 (2') cooling the liquid condensation reaction mixture effluent from the reactive stripping apparatus in a crystallizer to form a slurry containing crystals of the adduct of bisphenol-A and phenol in 1:1 molar ratio and the mother liquor, said crystallizer having two filter means provided therein whereby a portion of the slurry containing fine adduct crystals of bisphenol-A and phenol having a particle size less than that of predetermined crystal cut is allowed to pass alternatively through one of filter means with a circulating pump and is then introduced into at least one fine crystal destructor from which a solution obtained after destruction of fine crystals is returned to the crystallizer alternatively through the other filter means with said or another circulating pump,
 (3) separating the adduct crystals from the mother liquor optionally followed by washing the separated adduct crystals,
 (4') removing phenol from the adduct crystals obtained in step (3) above by introducing the adduct crystals into a vacuum or inert gaseous flow dephenolizer, bringing the adduct crystals to a temperature below the melting point thereof in vacuum or in the presence of an inert gaseous stream to decompose the crystals into a gas phase and a solid phase, withdrawing the gas phase in vacuum or with the inert gaseous stream and discharging the solid phase as high purity bisphenol-A crystals,
 (5) recrystallizing the high purity bisphenol-A crystals obtained in step (4) above in the presence of solvent in a recrystallizer, and
 (6) separating the bisphenol-A crystals from the mother liquor optionally followed by washing the separated bisphenol-A crystals to obtain an ultrapure bisphenol-A product.

According to yet another preferred embodiment of the present invention, a process for producing bisphenol-A is provided, comprising reacting acetone and phenol to form a reaction mixture containing bisphenol-A and water, cooling the remainder of the reaction mixture to form bisphenol-A -phenol adduct crystals, separating the adduct crystals from the mother liquor, and removing phenol from the adduct crystals to obtain bisphenol-A, characterized in that the reaction of acetone and phenol is conducted in a reactor column having a plurality of perforated trays supporting a solid particulate catalyst, and an inert gas is passed upward through the reactor column during reaction in order to agitate the catalyst while stripping the water from the reaction mixture, thereby forming a reaction mixture effluent having a reduced water content.

In a particularly preferred form, the latter embodiment of the invention is characterized in that during the cooling step, the reaction mixture effluent is cooled in a crystallizer containing at least first and second filter means, and a portion of the crystallized reaction mixture which has a particle size less than that of a predetermined crystal cut is pumped through the first filter means and is then introduced into a crystal destructor to obtain a dissolved solution which is returned to the crystallizer through the second filter means, the direction of circulation through the filter means being reversed after a predetermined period of time in order that a portion of the crystallized reaction mixture is pumped through the second filter means before being introduced into the crystal destructor and is returned to the crystallizer through the first filter means.

In an even more preferred form, this embodiment of the invention is further characterized in that phenol is removed from the adduct in a vacuum dephenolizer or a pneumatic dephenolizer having an inert gas flow.

According to the present invention, phenol and acetone are reacted in very good yields and excellent selectivity to bisphenol-A in a substantially vertical, multiple stage suspended reactive stripping apparatus.

The bisphenol-A concentration in the reaction mixture is increased to more than 25% and the concentration of by-products is relatively low according to the present invention. The reaction mixture can be crystallized without being concentrated, which not only ensures good product quality but also simplifies the process. The fine crystal destruction technique is applied in adduct crystallization stage to improve the crystal size and the size distribution in order to obtain high purity and uniform size adduct crystals. The gas-solid dephenolization technique is applied in crystal dephenolization stage for keeping relatively low dephenolization temperature to prevent bisphenol-A from becoming colorful and being decomposed. High purity bisphenol-A is obtained from the dephenolization stage without further purification.

Ultrapure bisphenol-A is obtained by recrystallizing the high purity bisphenol-A crystals with a solvent. The melt of secondary adduct crystals is mixed with reaction mixture issued from the condensation reaction stage after being washed with the washing medium from the washing step of the primary crystals and then recycled to the primary crystallizer. Therefore, the essential process stream has a low by-product concentration and is not contaminated with coloring substances.

BEST MODE FOR CARRYING OUT THE INVENTION

Figure 1:
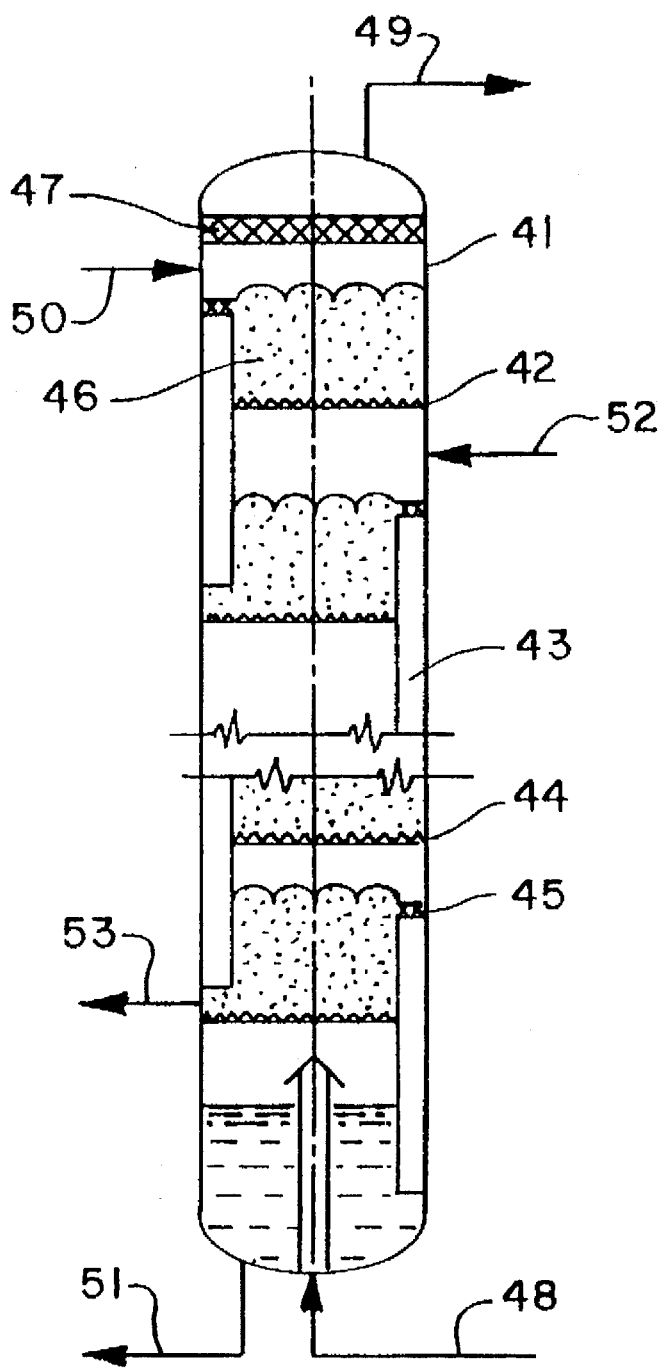
FIG. 1 is a schematic diagram of a novel multiple stage suspended reactive stripping process and apparatus showing various trays having a catalyst supported on each tray according to the present invention.

The present inventors have found that phenols, examples of which are alkyl phenols such as tertiary butyl phenol and 2,6-ditertiarybutyl paracresol and many hindered phenol antioxidants such as antioxidants 1010,168 usable in polyolefins, should have extremely good color when used. It is further in general recognized that the measures for obtaining good color are to avoid oxygen, to reduce temperatures used in the reaction and subsequent treatments and to decrease time of thermal effect to as minimum extent as possible. As a phenol type material, it is highly important in the production of bisphenol-A to completely avoid oxygen and to minimize thermal effect.

The production of bisphenol-A from the condensation reaction of phenol and acetone is carried out in the presence of a catalyst optionally also including a promotor. In the prior art, reaction and distillation are combined in a distillation reactor system to withdraw by fractional distillation one of the reaction products once it is formed during the reaction whereby yields of the desired product or conversion of feedstocks are enhanced to a great extent. Heretofore, fixed bed reactor systems are usually used in the production of bisphenol-A and conversion of acetone is only about 50% by weight in a single pass. Therefore, it was ever expected to apply the known distillation reactors in the production of bisphenol-A in order to enhance conversion of acetone and to obtain decrease in energy consumption, recycle quantity, material especially bisphenol-A product loss and volume of equipment.

Though reactive distillation is theoretically considered to be valuable the practical application of distillation reactor systems is very limited. As a typical example, reactive distillation systems are used to produce MTBE and low molecular weight esters in distillation reactor systems, but they are rarely used in other industries. They have not yet been used in reactions such as amidation, hydrogenation and methoxylation though they are theoretically applicable thereto. Difficulty is always encountered in that there is great difference between temperatures at which catalyst shows activity and boiling points of reaction mixtures.

For instance, temperatures at which catalyst is active in the condensation reaction for the production of bisphenol-A generally range from about 60° C. to about 100° C. with 120° C. being the highest. At these temperatures and the pressures involved, excess or unreacted phenol and water, etc. can not boil and therefore can not be distilled out from the reaction system. Otherwise, if higher temperatures are used, catalyst is susceptible to deactivation or further complete destruction because it may be softened or aged and the like whereas the boiling temperature of the reaction mixture of phenol, reaction products and by-products is higher than 180° C. Obviously, distillation reactor systems are not usable in the production of bisphenol-A. In view of the reaction kinetics, water formed during the condensation reaction suppresses the reaction rate. In known processes, water is taken out from reaction systems using a semipermeable membrane or a dehydrating agent or the like which have been described in the literature such as, for example the above-mentioned patents.

Unexpectedly, it has now been found that water generated during the condensation reaction of phenol and acetone may be stripped out from the reaction system at reaction temperatures which are below the boiling point of water, such as about 80° C. using an inert gaseous stream. The experiment in this respect shows that quantity of the inert gaseous stream necessary for removal of water generated during the condensation reaction is not large and it proves industrially practicable.

An ion-exchange resin catalyzed process for the production of bisphenol-A has generally a selectivity to the desired product, i.e.p, p-bisphenol-A of about 80% by weight. While a large amount of the isomers produced during the condensation reaction is recycled to the reaction system in which the ratio of the recycle amount to main flow fed to the reaction system may be up to 0.7:1 in order to inhibit formation of further isomers, the disadvantages involved in this embodiment are obvious. However, the selectivity to the desired product (p,p-bisphenol-A) may be more than about 90% in a single pass through a specifically designed multiple stage suspended reactive stripping apparatus. As already established in the prior art, an increase in the ratio of phenol to acetone may undoubtedly improve the selectivity to p,p-bisphenol-A though theoretical ratio thereof is 2:1. In general, the selectivity to the desired product may be enhanced when using phenol/acetone ratio of 8–10:1. Nevertheless, the present inventors found that a dropwise addition of acetone to the reaction system under conditions of strong or intensive agitation by the action of said inert gaseous stream always results in good selectivity to the desired product and excellent conversion of acetone. Under these conditions, the condensation reaction is carried out in a batch process.

Although not to be bound by any theory, it is appreciated that extremely high ratio of phenol to acetone may be obtained at any moment through all the condensation reaction by means of dropwise addition of acetone according to the present invention. Accordingly, the present inventors understand the concept of "time series" which has been established in the control theory by Norbert Wiener. CYBERNETICS, 1961. According to Wiener, all of procedures occurring over time may be described as "time series". All of batchwise operations are procedures occuring over time. However, any process which is to industrialized must be continuously carried out on a large scale. Therefore, "time series" established by Wiener must be converted to "space series". That is to say, it is necessary to provide a multiple stage arrangement for realization of extremely high ratio of phenol to acetone in the case in which bisphenol-A is desirably produced whereas overall ratio of phenol to acetone should be as small as possible in order that the concentration of bisphenol-A is remarkably enhanced and the recycle flow is significantly reduced. Thus, it is required to charge acetone feedstock to the reaction system in a highly dispersible manner. Nevertheless, operation, control and structure of equipment will be undoubtedly complicated in the case in which there are used too many positions for entry of feedstocks.

In order to overcome these disadvantages, the present inventors have developed a novel process comprising charging all of the required phenol above the uppermost or first perforated tray, immediately followed by staged addition and atomization of acetone and simultaneous introduction of an inert gaseous stream which rises through a plurality of perforated trays having catalyst particles supported thereon. Atomized acetone is absorbed into the suspension of particulate catalyst in the liquid phase of the reaction system in association with the rising inert gaseous stream while the acetone reacts with phenol in the presence of the catalyst. Since the dispersity of molecules of acetone in the form of vapor is millions upon millions of times that of liquid drops, extremely high ratios of phenol to acetone are obtained at any point of the reaction system within all the space of the reactor column at any time. This inventive concept obviously applies to the industrial enlargement based on a number of small scale reactions performed in the manner of dropwise introduction of feedstocks.

In accordance with this novel process, the content of impurities present in the reaction mixture effluent from the inventive multiple stage suspended reactive stripping apparatus is in the order of hundreds of ppm and therefore complicated purification of bisphenol-A as reaction product can be substantially avoided. The purity of primary bisphenol-A adduct crystals may be up to about 99.99% and recrystallization of the adduct crystals is of course unnecessary in this case.

The impurity content of the mother liquor is present at a very low level though the impurities are accumulated to some extent. The mother liquor may be subjected to secondary crystallization. It is unnecessary to recycle isomers of p,p-bisphenol to the condensation reaction for the purpose of inhibiting further formation thereof. As a result, it is also not necessary to return the mother liquor to the reactive stripping apparatus although it is also acceptable to do so as hereinafter described.

More importantly, it is completely unnecessary to concentrate the liquid reaction mixture effluent from the reactive stripping apparatus before it is subjected to primary crystallization. Further, recovery of acetone is also omitted owing to high conversion of acetone feed.

In the prior art processes for the synthesis of bisphenol-A, a semipermeable membrane and the like as a dehydrating means may be used to increase the concentration of bisphenol-A product in the reaction mixture from the condensation reaction. Reference may be made to U.S. Pat. Nos. 5,087,767 as mentioned above. However, the reaction procedure is too complicated to be industrialized on a large scale.

In general, the concentration of BPA in the reaction mixture effluent is in the order of about 15% by weight in the widely used ion-exchange resin catalyzed processes for the synthesis of BPA. If this reaction mixture is directly subjected to crystallization, yields of the bisphenol-A adduct crystals would be as low as from about 30% to about 40% by weight. In addition, conversion of acetone is around 50% by weight and the reaction mixture contains an important amount of unreacted acetone. Obviously, it would be disadvantageous to provide no operations for removal of light or lower boiling components such as $H_2O$ and acetone and subsequent separation of acetone from water.

In surprise, it is now found that the reaction mixture issued from the novel reactive stripping apparatus has a bisphenol-A content of more than about 30% by weight and, after the addition of recovered bisphenol-A in the secondary crystallization, may amount to about 35% by weight. Such a reaction mixture is directly subjected to crystallization. Advantages resulting from omission of the intermediate step involving concentration of the reaction mixture are remarkable. For example, energy consumption and operation installations are significantly reduced. What is more important is that the bisphenol-A product is protected against the adverse thermal effect in the concentration, thereby notably improving color level of the bisphenol-A product. Accordingly, the present invention is distinctively different from present commercial processes for the synthesis of bisphenol-A such as those mentioned above.

Furthermore, it was found through experiment, to the inventor's astonishment, that color quality would be deteriorated by several APHA if the reaction mixture from a condensation reactor is concentrated. Therefore, by omission of intermediate concentration of the reaction mixture, the present invention can improve color level of bisphenol-A product at least by several APHA correspondingly. In effect, the color level of the bisphenol-A product obtained in accordance with the present invention may be as low as 7 APHA and even 4 APHA.

On a preferred embodiment of the present invention, particulate catalyst is placed on a plurality of screens supported on a plurality of trays. The catalyst is present in the form of substantially homogeneous mixture in the liquid reaction mixture under agitation of the rising inert gaseous stream. This is in contrast to performance of conventional reactor systems for example those mentioned above wherein catalyst is blocked in a mesh container or pocket with strong resistance for transfer of acetone to the boundary (catalytic site) between the liquid phase (phenol and acetone) and the solid phase (catalyst). In the present invention, such a resistance to mass transfer is significantly reduced because of arrangement of novel multiple stage suspended reactive stripping apparatus and agitation action of the inert gaseous stream.

It is operation of the multiple stage suspended reactive stripping apparatus by making use of an inert gaseous stream as a stripping medium that results in good conversion of acetone, such as about 99.9% or more, and excellent selectivity to the desired product, for example the selectivity to bisphenol-A of from about 96 to about 97% at about 80° C. and about 99.7% at about 60° C. Nevertheless, the content of bisphenol-A in the reaction mixture is low at lower temperatures, e.g. 60° C. or less. Accordingly, preferred temperatures range from about 60° C. to about 130° C., prefererably from about 80° C. to about 100° C. in the reactive stripping apparatus. If the reaction temperature is higher than about 130° C., the catalyst will be completely destroyed.

Similarly, in a preferred embodiment of the present invention, the preferred molar ratio of phenol to acetone ranges appropriately from about 4:1 to about 12:1. If the ratio is lower than about 4:1, the selectivity to bisphenol-A will be reduced greatly. In contrast, if the ratio is more than about 12:1, the recycle quantity of phenol is too great to be economic.

The present invention will hereinafter be described in more detail with reference to the attached drawings.

Figure 2:
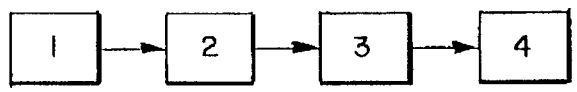
FIG. 2 is a schematic flow diagram for the production of high purity bisphenol-A according to one of embodiments of the present invention including a novel reactive stripping process.
Figure 3:
FIG. 3 is a schematic flow diagram for the production of high purity bisphenol-A according to another embodiment of the present invention including a novel reactive stripping process and a novel process for the destruction of fine crystals.
Figure 4:
FIG. 4 is a schematic flow diagram for the production of high purity bisphenol-A according to a further embodiment of the present invention including a novel reactive stripping process and a novel process for the vapor-solid removal of phenol.
Figure 5:
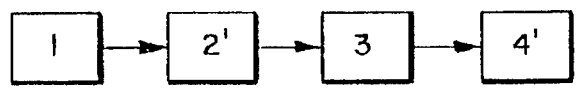
FIG. 5 is a schematic flow diagram for the production of high purity bisphenol-A according to a still further embodiment of the present invention including a novel reactive stripping process, a novel process for the destruction of fine crystals and a novel process for the vapor-solid removal of phenol.
Figure 6:
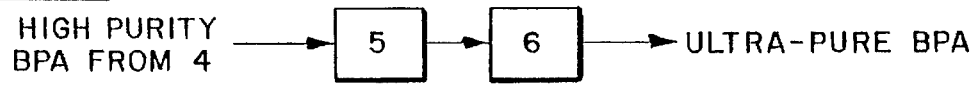
FIG. 6 is a schematic flow diagram for the production of ultrapure bisphenol-A according to a still further embodiment of the present invention including the recrystallization of high purity crystals of bisphenol-A.
Figure 7:
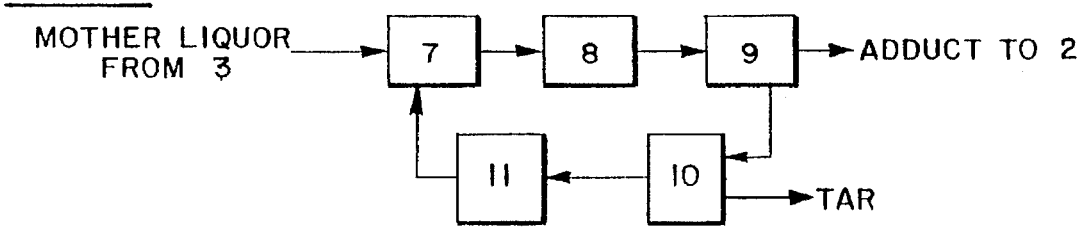
FIG. 7 is a schematic flow diagram showing treatments of the mother liquor from which adduct crystals of bisphenol-A and phenol have been separated in step (3) of a process for the production of high purity and ultrapure bisphenol-A according to the present invention.

In step 1, as shown in FIG. 2 phenol is reacted with acetone in a novel, substantially vertical, multiple stage suspended reactive stripping apparatus to produce bisphenol-A. The reaction is catalyzed with a modified cation-exchange resin. According to a preferred embodiment of the present invention, the molar ratio of phenol to acetone can be significantly decreased while the conversion of acetone and the selectivity to bisphenol-A can be increased greatly both of which may be at least about 96% by weight and may be up to about 99.9% by weight in a single pass. Bisphenol-A concentration in the reaction mixture is more than 25% by weight. This reaction mixture can be crystallized directly to produce adduct crystals of bisphenol-A and phenol in 1:1 molar ratio without being intermediately concentrated. The content of by-products in the reaction mixture is relatively low because of high selectivity to the desired product, i.e. bisphenol-A. All these advantages are attributed to use of the reactive stripping apparatus provided by the present inventors.

The apparatus used for the operation of reactive stripping according to the present invention is also referred to as multi-stage suspended bed for the reactive stripping. According to the present invention, the apparatus includes a reactor column containing a plurality of trays vertically spaced from one another. The trays are interconnected by downcomers for conducting liquid downward from tray to tray. Sieve screens are placed on every trays, and a solid particulate catalyst having a diameter more than the sieve mesh of the screen is carried on the sieve screens directly. The openings of the downcomers are enclosed with the same sieve screens. An inert gaseous stream enters the reactor column from the gas inlet at the reactor bottom, and rises upwardly through the liquid layers on the trays, and leaves from the gas outlet at the reactor top. There is at least one liquid feedstream inlets at the reactor top, and there are several side feedstream inlets at different heights along the wall of the reactor column above the lowermost tray, and there is a liquid product outlet at the bottom of the reactor column. There is a side pipe for each tray to withdraw the used or deactivated catalyst and introduce fresh and/or the regenerated catalyst. The trays provided in the reactive stripping column are sieve trays, float valve trays or any other suitable gas-liquid contact trays.

The present continuous process of reaction between phenol and acetone for preparing bisphenol-A in the presence of an ion-exchange resin as a catalyst is characterized in that the reaction is performed in a novel multiple stage (bed) reactive stripping apparatus instead of the fixed-bed reactor. All of phenol necessary for the reaction is charged from the liquid feedstream inlet at the reactor top and acetone is charged from the several side feedstream inlets. Use of the novel reactive stripping apparatus overcomes the aforementioned disadvantages.

According to the present invention, the effect of the inert gas or gaseous stream, the perforated trays and side acetone inlets may be summarized in a preferred embodiment of the present invention for performing the reaction between phenol and acetone as follows:

The effect of the rising inert gas is to prevent leakage of the reaction liquid through the sieve screens, which are located on the trays thereby maintaining a certain height of the reaction liquid on each tray and quickly reacting phenol and acetone on the trays, to allow the resin catalyst particles to be suspended in the reaction liquid layers on the trays owing to the agitation of the inert gas so that each tray is equal to an ideal mixing tank, the whole reactor being equal to a lot of tanks in series and the resistance to the mass transfer that affects the reaction is reduced greatly, and to remove water generated during the reaction between phenol and acetone with the inert gas through bubble contact of the inert gas with the reaction liquid.

The effect of the perforated trays is to confine the backmixing zone of the reaction liquid to one tray, thereby fully utilizing the higher reaction rate of the beginning or upper trays, to supply the required gas-liquid mass transfer area in order to remove water generated during the reaction from a mixed solution containing acetone, phenol and bisphenol-A product, and to reduce the static liquid level on the trays, thereby allowing the resin particles to be uniformly suspended in the liquid.

The effect of the several side inlets for acetone feedstream is to maintain a high relative phenol concentration in individual chambers whereas the overall phenol/acetone feed molar ratio is relatively low, thereby enhancing the reaction selectivity to bisphenol-A and reducing the phenol recycle amount, and to allow higher reaction temperatures to be employed.

Referring first to FIG. 1, the novel multiple stage suspended reactive stripping apparatus for continuously carrying out chemical reactions while separating at lease one lower boiling component from the reaction mixture or the reaction system includes a reactor column 41 with a plurality of vertically spaced trays 42. A downwardly flowing liquid flow path is provided between the trays by downcomers 43. Sieve screens 44 are placed on the trays, all of the top openings of the downcomers are enclosed by the same sieve screens 45 as those placed on the trays. Sieve screens 44 and 45 are constructed of, for example, stainless steel or another material, which will not be affected under the reaction conditions. Particulate catalyst 46 (shown in the suspended state) having a larger diameter than the sieve mesh is located on the trays. There is a liquid entrainment catching structure 47 in the upper section of the reactor column. No. 48 and No. 49 designate the inert gas inlet and outlet, respectively. No. 50 and No. 51 designate the liquid reactant inlet and liquid reaction mixture outlet, respectively. Along the reactor side wall there are several side reactant inlets 52 and a side pipe 53 for withdrawing the used particulate catalyst from each tray and charging fresh particulate catalyst and/or the regenerated catalyst.

As shown in FIG. 1, there are at least two perforated trays 42 in the reactor column. Of course, the more trays 42 are used, the better efficiency will be obtained but the expenditure of capital on the equipment will be thus increased. The porosity of the trays 42 is usually from about 1 to about 50%, preferably from about 10 to about 30%. The mesh of the screens 44 depends on the particle size of the particulate catalyst 46 but the former is always slightly smaller than the latter. The downcomers 43 all have the screen caps 45 located on the ends thereof and the caps 45 may be connected to the downcomers 43 in any conventional manner such as by means of welding. The cap screens 45 are constructed from the same material as the screens 44 which are placed on the trays 42. The length of each downcomer 43 above the tray associated therewith is from about ½ to about ¾ of the height between adjacent two trays 42.

The pressure in the reactor column is atmospheric pressure or a slightly elevated pressure. The proportions of various portions of acetone respectively charged to the reactor column 41 are determined depending predominantly on the desired yields of the selectivity to bisphenol-A. The number of trays 42 above which acetone is charged or the number of the side acetone inlets also depends on the desired yields of and selectivity to bisphenol-A. Of course, the more the acetone inlets, the more complicated the structure of the reactor column. In a preferred embodiment of the present invention, there is at least one tray 42 between two adjacent side acetone inlets though it is possible to provide an acetone inlet above every tray 42. More preferably, there are from 1 to 5 trays between two adjacent side acetone inlets in the practice of the present invention. The acetone feedstream may be in the form of vapor or liquid or mixture thereof.

The inert gaseous stream useful for taking at least one lower boiling component or product out of the reaction mixture may be any commercially available inert gas such as nitrogen or argon or any mixture thereof and nitrogen is particularly preferred because of availability and economy.

In accordance with the reactive stripping process of the present invention the overall phenol/acetone feed molar ratio may be about 4–12:1, more preferably is about 7–10:1 and most preferably is about 7:1. The reaction temperature may be from about 60° C. to about 130° C., preferably from about 80° C. to 100° C. and the residence time calculated on the basis of dry catalyst weight is from about 0.25 to about 2 hrs. The reaction pressure is atmospheric or a slightly elevated pressure. The velocity of the rising inert gas is from about 0.006 to about 0.075 m/s based on the area of the column cross-section. The catalyst loading for each tray or chamber is in the range of from about 3% to about 10% by volume of the total volume of the whole mixture including the catalyst and reaction liquid.

The inert gaseous stream from the gas inlet 48 flows countercurrently relative to liquid streams which enter through liquid reactant inlet 50 and side reactant inlets 52. The reaction between excess phenol from liquid reactant inlet 50 and acetone from side reactant inlets 52 takes place in the liquid-solid suspension on the trays 42. The above-described multiple stage reactive stripping process and apparatus according to the present invention have the following advantages:

Due to the stir of the inert gas, the particulate catalyst is suspended in the reaction liquid in the reactor column, so the resistance to the diffusion of reactants toward the catalyst surface is reduced and the reaction rate is increased greatly.

The inert gas removes water from the reaction liquid, and as a result, the catalyst maintains a high activity and the reaction rate is further increased. In contrast, in a conventional system, water will poison the catalyst.

Use of multiple acetone injection points in the ion-exchange resin catalyzed BPA synthesis process allows a high relative phenol concentration to be maintained at each individual tray in order that high purity and ultrapure BPA can be prepared at a lower overall phenol/acetone feed molar ratio.

The stirring effect and heat transfer effect of the inert gas can reduce the column's axial and diametrical temperature differences brought about by exothermal reaction, so the local overheating can be avoided and the optimum reaction conditions can be controlled easily.

For each tray of the reactor column there optionally can be a side pipe by which the resin can be added to or removed from the tray.

Thus, the catalyst can be changed tray by tray, and it is therefore unnecessary to have a spare column. Furthermore, it is possible to operate the column continuously even when the catalyst on one tray is being changed.

In accordance with the present invention, a condensation reaction liquid with a high BPA concentration is obtained. This liquid can be directly transported to a crystallizer to produce a slurry of 1:1 molar ratio phenol/BPA adduct crystals in mother liquor. Thus, before the tallization, the operation of removing acetone, water and some phenol in a concentrator by evaporation can be eliminated from the BPA production process. This elimination results in a substantial increase in the quality of the bisphenol-A product.

The lower overall phenol/acetone feed molar ratio reduces the volume of the unreacted phenol recycle stream, and therefore, the burden for the process after the condensation reaction is lightened.

The requirement for a suitable pair of the liquid boiling point and catalyst activity temperatures imposes limits on the efficient use of a distillation reactor column. According to the present invention, because the more volatile component is removed from the reaction liquid by an inert gas, there is no requirement for a temperature match for the reaction and separation processes.

In accordance with the process of the present invention, the BPA concentration in the condensation reaction liquid can reach 30% by weight or more, the conversion of acetone may be about 96% or more, and selectivity to BPA may be about 95% or more on the average in a single pass.

According to the present invention, the catalyst used in carrying out the reactive stripping process for the production of bisphenol-A may be any strong acid ion-exchange resin catalyst conventionally used in this respect. Preferred are sulfonic acid ion-exchange resin which may be optionally modified with a mercaptoamine.

As shown in FIGS. 2–7, the reaction mixture from condensation reaction step 1 is directly introduced into primary crystallization step 2 or 2' or a primary crystallizer for precipitating bisphenol-A in the form of adduct crystals of bisphenol-A and phenol in 1:1 molar ratio. The concentration of bisphenol-A in the reaction mixture being passed to a crystallizer is from about 25% to about 45% by weight, preferably from about 30% to about 40% by weight, more preferably from about 30% to about 35% by weight and most preferably from about 30% to about 33% by weight.

The primary crystallization of bisphenol-A may be performed in any conventional manner. During the primary crystallization in accordance with the present invention, however, a fine crystal destuction technique which is also part of the present invention may be employed to modify the crystal size and the size dinn thereby reducing the entrained mother liquor content in the adduct crystals of bisphenol-A and phenol so that a high purity adduct crystals can be obtained. In addition, the efficiency of successive filtration and washing of the adduct crystals which will be hereinafter described in detail may be improved greatly by making use of the fine crystal destruction technique.

Another aspect of the present invention is to provide a novel method for the preparation of bisphenol-A product with high purity by applying a fine crystal destruction technique. Thus, the present invention furthermore provides a novel method for preparing crystalline bisphenol-A/phenol adduct with large and uniform crystal size. In order to practice this preferred method, A. two filters are installed in a crystallizer;

B. a part of slurry containing crystalline bisphenol A/phenol adduct is drawn from the crystallizer and filtered through the first filter by using a circulating pump, and a slurry containing only fines of size smaller than the fine crystal cut size is fed into at least one fine crystal destructor, then the solution in which the fines have been destructed is fed back to the crystallizer through the second filter to wash the second filter and further crystallize;

C. after a switching interval, a part of slurry containing crystalline bisphenol-A/phenol adduct is drawn from the crystallizer and filtered through the second filter by using the circulating pump, and a slurry containing only fines of size smaller than the fine crystal cut size is fed into at least one fine crystal destructor, then the solution wherein the fines have been destructed is fed back to the crystallizer through the first filter for washing the first filter and further crystallization in the crystallizer;

D. after a switching interval, repeating the procedure B and washing the second filter, thereby repeating the procedures B and C alternatively to carry out the fine crystal destruction process continuously.

The crystallizer used in the present invention includes various types and configurations of crystallizer. The preferred crystallizers include cooling crystallizer, such as stirring crystallizer, Swenson-Walker crystallizer and Cerny direct-coolant crystallizer; evaporating crystallizer; salting crystallizer; reaction crystallizer and vaccum crystallizer, etc.

The filters used in the present invention comprise various types and configurations of filters being able to allow fines of size smaller than the cut size to pass through, for example, porous hollow cylinder, spheroid-and table-types of sterofilter covered with or without filter cloth. The most preferred filter is a filter consisting of a porous hollow cylinder covered with knitmesh materials. Said hollow cylinder can be made of metal, ceramics or polymer, depending on the treated materials. The knitmesh materials can be made of metal wire or glass fiber, or a kind of fabric made from synthetic fiber or natural fiber such as cotton, wood, silk, hemp, etc. Said knitmesh has a definite pore size to allow the crystals of size smaller than the cut size to pass through, which is decided by the fine crystalcut size, i.e. the maximum size of the fines expected to be destructed. The fine crystal cut size can be controlled by using knitmesh materials with different pore sizes to cover the porous hollow cylinder. The most preferred knitmesh material in the present invention is a metal screen.

The filter can be installed at any location below the liquid level of the slurry, preferably the two filters are substantially immersed vertically and oppositely in the upper part of the slurry.

The fine crystal destructors used in the present invention are heat-exchangers being able to dissolve the fines by heating, preferably shell and tube exchanger, coil heat exchanger or jacketed heat exchanger, etc.

In the present method, either one or two fine crystal destructors may be used, depending on the performance of the circulating pump itself and the influence of the crystals on the circulating pump. When two fine crystal destructors are used, they may or may not be the same, and the circulating pump is installed between the two fine crystal destructors. When one destructor is used, the circulating pump may be installed either before or behind the destructor.

The present method is suitable for either a continuous or a batch crystallization process. The circulating amount of the slurry is determined by the crystallization system and the desired crystal size distribution of the crystalline product. In general, the circulating amount of the slurry in a continuous crystallization process is from about 3 to about 10 times of the handling capacity of the crystallizer while in a batch crystallization process the circulating amount is from about ⅙ to about ¼ of the loading amount of the crystallizer. The time of the circulation is equal to the time of crystallization.

The present invention is illustrated in more detail with reference to FIG. 8.

Figure 8:
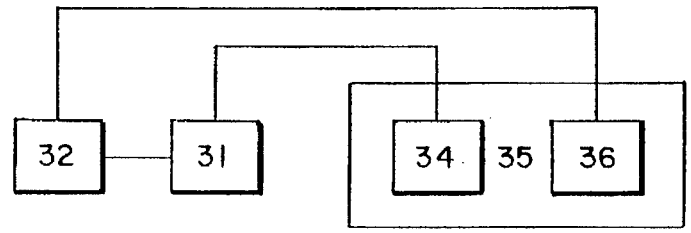
FIG. 8 is a schematic flow diagram illustrating crystallization of the reaction mixture from a reactive stripping apparatus with destruction of fine crystals according to the present invention.

In FIG. 8, a slurry containing only the fines of size smaller than the fine crystal cut size is drawn from crystallizer 35, through filter 34 in crystallizer 35, to fine crystal destructor 31 wherein the fines are dissolved by heating, then passed with a circulating pump 32 to filter 36 located in crystallizer 35, thereby washing filter 36, and finally back to crystallizer 35. After an interval, the above-mentioned process runs in the opposite direction, i.e., the slurry containing only fines of size smaller than the fine crystal cut size is drawn from crystallizer 35, through filter 36 in crystallizer 35 and circulating pump 32 to fine crystal destructor 31, then passed through filter 34 in crystallizer 35, thereby washing filter 34, and finally back to crystallizer 35. The above-mentioned process is switched over at regular intervals and run continuously.

Comparing with the prior art, the present invention has the following advantages:

1. Through a filter installed in a crystallizer, a slurry containing only fines of size smaller than the fine crystal cut size is drawn from the crystallizer, through a fine crystal destructor wherein the fines are dissolved and back to the crystallizer. The above process is simple and effective, not requiring any change of the original crystallizer. The fine crystal cut size can be controlled by selecting the covering knitmesh materials with different pore sizes.

2. There are two filters in the crystallizer. The slurry is drawn from one filter to a fine crystal destructor for dissolving fines, then through another filter to wash the latter and finally fed back to the crystallizer. The two filters are switched over and washed at regular intervals to prevent blockage and ensure the continuous operation of the process.

3. There may be a fine crystal destructor at each side before and behind the circulating pump. This arrangement keeps crystals from entering the circulating pump and hence the requirement to the performance of the pump is less hard.

4. The crystal size and its distribution obtained in the crystallizer can be effectively controlled by regulating the flow rate of the circulating fine crystal slurry, and a crystalline product with uniform, large crystal size and high purity can be obtained.

The effluent discharged from primary crystallization step 2 or 2' or primary crystallizer is a slurry containing the adduct crystals and mother liquor. The slurry is then introduced into solid-liquid separation step 3 in which the adduct crystals are separated from the mother liquor and then optionally washed.

The separation of the adduct crystals from the mother liquor may be carried out in any conventional methods. The exemplary methods usable in the present invention are filtration and centrifuge, etc.

The separated adduct crystals are optionally washed with a solvent which is preferably phenol, more preferably that obtained in the successive step of removing phenol from the adduct crystals which will be hereinafter described in detail. The weight ratio of washing solvent to the adduct crystals preferably ranges from about ¼ to about ½. The temperature during the washing step is from about 40° C. to about 50° C.

The moisture content of the separated and optionally washed adduct crystals from solid-liquid separation step 3 is less than about 30% by weight, preferably less than 15% by weight. These adduct crystals enter step or dephenolizer 4 or 4' in which phenol is separated from bisphenol-A. Phenol to be removed from the adduct crystals may be free and associated with bisphenol-A in the adduct crystals.

The dephenolization of the adduct crystals may be carried out in any conventional manner. Nevertheless, a novel gas-solid dephenolization technique which is also part of the present invention may be used to nearly completely, i.e. one hundred percent remove phenol including free phenol and associated phenol from the adduct crystals. The gas-solid dephenolization may be conducted in vacuum or in an inert gaseous stream in a dephenolizer. The temperatures for the removal of phenol ranges from about 60° C. to about 130° C., preferably from about 80° C. to about 110° C.

In the known processes of removing phenol from the adduct crystals, problems are inevitably encountered such as lower yields and quality (such as color level) of bisphenol-A due to the high temperatures or the increase of capital and operation costs of solvent recovery and the like by recrystallization, distillation or steam stripping methods. There is also great difficulty in the waste water treatment for steam stripping method.

In order to avoid heating the adduct crystals at higher temperatures, to decrease the capital and operation costs and to obtain a high purity and ultrapure bisphenol-A product, the present inventors develop a novel process of gas-solid dephenolization which takes place at low temperatures.

The adduct of bisphenol-A with phenol is an unstable crystalline compound which tends to decompose when heated. In the presence of vacuum or an inert gaseous stream, when heated below its melting point, the adduct crystals decompose to form bisphenol-A solid and gaseous phenol and when heated above its melting point, the adduct crystals melt. The present inventors unexpectedly discovered that the decomposition pressure of the adduct crystals of bisphenol-A with phenol is considerably greater than the saturated vapor pressures of liquid phenol and the mixture solution of phenol and bisphenol-A, which demonstrates that the adduct crystals of bisphenol-A with phenol can decompose at relatively lower temperatures while phenol can be removed. As is proven by experiment, bisphenol-A is highly sensitive to oxygen. The present inventors have developed a method of removing phenol under vacuum or by an inert gaseous stream in a gas-solid reaction of the adduct crystals in order to complete the invention of directly obtaining high purity bisphenol-A from the adduct crystals at lower temperatures.

According to a preferred embodiment of the present invention, there is provided a process for producing high quality bisphenol-A by removing phenol from the adduct crystals of bisphenol-A and phenol which process employs neither solvent or water nor any high temperature procedure. Instead, the dephenolizing process of the present invention utilizes the gas-solid reaction to remove phenol from the adduct crystals and to directly obtain high quality bisphenol-A.

According to a further preferred embodiment of this invention, there is provided a process for producing high purity bisphenol-A by removing phenol from the adduct crystals of bisphenol-A and phenol, comprising directly feeding the adduct crystals into a vacuum or pneumatic dephenolizing device under vacuum or in the presence of an inert gaseous stream, controlling the temperature of the adduct crystals below the melting point of the adduct crystals, decomposing the adduct crystals to a gas phase and a solid phase, the gas phase phenol being removed from the dephenolizing device under vacuum or by an inert gaseous stream out of which the phenol is then condensed and recovered, thereby obtaining a high quality bisphenol-A product directly from the dephenolizing device.

In the dephenolizing process of the present invention, the moisture content of the adduct crystals should be controlled below about 30% by weight, preferably below about 15% by weight and a lower moisture content is preferred. The device in which dephenolization is conducted can be a commercially available vacuum or pneumatic device such as, for example, a cylindrical vacuum desiccator, vacuum oven or fluidized reactor. Under vacuum or in the presence of an inert gaseous stream, the feedstock can be at the static or fluidized state. As operating medium, the inert gaseous stream includes any gaseous streams which are unreactive to bisphenol-A and phenol as well as the adduct crystals thereof, such as nitrogen and argon, preferably nitrogen. A heat exchanger means should be installed inside the dephenolizing device to supply the heat needed in the gas-solid dephenolizing reaction. The temperature of the adduct crystals is controlled between about 40° C. and about 130° C.

The adduct crystals decompose to form two phases when heated, wherein bisphenol-A forms the solid phase, and phenol forms the gas phase. The gas phase of phenol is removed from the dephenolizing device under vacuum or by an inert gaseous stream and thus high purity bisphenol-A is directly obtained.

Both batch and continuous methods of operation can be used in the dephenolizing process of the invention. During the batch operation, the operating conditions of the vacuum dephenolizing device are as follows: the temperature ranges preferably from about 60° C. to about 130° C. The rising rate of temperature may be varied according to the required residence time, and is from about 0.2° to about 2.0° C./min with a preferred rate of about 1.2° C./min. The operating pressure is from about 2 to 50 torr and the residence time is from about 1 to about 4 hrs. During the batch operation, the operating conditions of the pneumatic dephenolizing device are as follows: the temperature ranges preferably from about 60° C. to about 130° C., and the maximum rising rate of temperature is about from 0.2° to about 2.0° C./min and preferably about 1.2° C./min, the residence time is from about 1 to about 3.5 hrs, and the flow rate of the inert gaseous stream is from about 0.1 to about 0.5 m/s.

During continuous operation, on the other hand, the operating temperature profile may be divided into at least two or three sections, e.g. the first is from about 60° C. to about 85° C., the second is from about 85° C. to about 110° C., and the third is from about 110° C. to about 130° C. The ratio of the operation times of the three sections is approximately 2:1:2, and the total residence time is from about 1 to about 4 hrs.

Compared to the known processes in the art such as those described in the above-mentioned patents, the dephenolization process of the invention has the following advantages:

1. It is not necessary for the adduct crystals to be dephenolized by distillation at high temperatures. The operating temperature is far below the decomposition temperature of bisphenol-A and no impurities and coloring substances are additionally formed, thereby obtaining the product bisphenol-A with high purity and low color level.

2. It is not necessary for the adduct crystals to be subjected to solvent extraction or recrystallization, thus the problem of a large amount of solvent recovery because of the dephenolization by solvent extraction or recrystallization is avoided. The dephenolization procedure of the present invention is simplified, and the capital and operation costs are substantially decreased.

3. The single pass yields for preparing bisphenol-A by decomposing the adduct crystals according to the dephenolization process of the invention are almost 100%.

The indexes of the product bisphenol-A obtained using the dephenolization process of this invention are as follows:

| | |
|---|---|
| purity | >99.95 by weight |
| melting point | >156.8° C. |
| free phenol | <100 ppm |
| ash content | <0.01% by weight |
| color (in 50% ethanol) | <10 APHA |
| iron content | <0.1 ppm |

The primary mother liquor from dephenolization step 3 is introduced into concentration step 7 in which the concentration of remaining bisphenol-A is enhanced. The concentrated mother liquor is then subjected to secondary crystallization in step or secondary crystallizer 8 to precipitate also bisphenol-A in the form of adduct crystals of bisphenol-A and phenol. The secondary adduct crystals are separated in step 9 and then may optionally be washed with the used washing liquid obtained in step 3. The separated secondary adduct crystals are returned to the condensation reaction mixture effluent issued from the reactive stripping apparatus. These crystals may be heated to become a solution before they are recycled to the reaction mixture from the reactor column. But this is not necessary since the temperature of the reaction mixture issued from the reactive stripping apparatus is sufficient to melt the crystals.

The secondary mother liquor discharged from separation step 9 may be subjected to cleavage or cracking operation step 10 which may be performed in any conventional manner for example that described in some of the above-mentioned patents or patent applications. Thereafter, tar generated during the cleavage operation is discharged from cleavage step 10 and then discarded. In this step, most of coloring substances and impurities which can not be recovered are discharged as tar out of the operation system.

In the operation of cleavage or cracking, o, p-bisphenol-A and remaining p,p-bisphenol-A present in the secondary mother liquor are cracked to recoverable phenol and para-isopropenylphenol(PIPH). Impurities that can not be cracked are discharged from the operation system as a tarry residue.

The residual solution containing phenol and para-isopropenylphenol resulting from the cleavage or cracking is introduced into a rearrangement means which may be any conventional reactor. In the rearrangement reactor, phenol and para-isopropenylphenol are reacted to produce the desired p,p-bisphenol-A. Thereafter, the solution containing the newly formed p,p-bisphenol-A is returned to concentration step 7.

Because the concentration of the by-produces including aromatic column substances in the secondary mother liquor is relatively high, the by-products in the secondary mother liquor entrained in the adduct crystals undoubtedly will contaminate the principal process stream to a considerable extent if the adduct crystals are recycled without being washed. This would be disadvantageous in the preparation of high purity bisphenol-A. Moreover, because the concentration of by-products in the primary mother liquor is much lower than the impurity content of the secondary adduct crystals, the liquid phenol which has washed the primary adduct crystals may be used to wash the secondary adduct crystals. With the primary and secondary adduct crystals being washed in such a procedure, the quantity of the washing liquid will not be increased and the amount of by-products which enter the principal process, including essentially the condensation reaction, primary crystallization, separation of primary adduct crystals and dephenolization, will be reduced to minimum level. This is an advantage of the present invention.

The purity of the bisphenol-A product obtained as described above is much higher than that obtained according to presently known processes. Therefore, the bisphenol-A product can be employed to manufacture polycarbonates of a quality which is necessarily much superior to that of polycarbonates made of known bisphenol-A products.

In order to obtain ultrapure bisphenol-A products, bisphenol-A recovered from dephenolization step 4 is subjected to recrystallization in step 5. The recrystallization of high purity bisphenol-A may be performed in the presence of solvent in any conventional manner. The solvent used therein may be toluene and water and other suitable solvents which are usually used for this purpose. The effluent from recrystallization step 5 is then introduced into separation step 6 in which bisphenol-A and the solvent are separated to obtain an ultrapure bisphenol-A product. in step 6, the separation may be carried out in the same manner as described above for step 3.

The bisphenol-A obtained as described above may has a purity of about 99.999% or more.

To illustrate more clearly the present invention and its advantages, the following examples are provided. Unless otherwise indicated, in the following examples as well as throughout the entire specification and in the following appended claims, all parts and percentages are expressed by weight and all temperatures are in terms of degrees centigrade.

EXAMPLE 1

The condensation reaction of phenol and acetone was carried out in a multiple stage suspended bed reactor column as described hereinbefore. The reactor has an internal diameter of about 150 mm, height of about 2200 mm, and is equipped inside with 13 perforated trays which are vertically spaced apart from each other by a distance of about 150 mm and have a porosity of about 20%. The perforated trays are covered with 60 mesh sieve screens on which are loaded a modified macroporous styrene-divinylbenzene strong acid ion-exchange resin catalyst. Phenol was fed into the reactor column from the uppermost tray and the feed rate was about 5.604 kg/hr. Acetone was fed into the reactor column in three sections above the second, the fifth and the tenth trays, respectively with the total feed rate of about 0.494 kg/hr, and the proportions of the three acetone portions on the second, fifth and tenth trays being about 15.79%: about 31.58%: about 52.63%, respectively. Recycle nitrogen was passed upwardly through the reactor column from the bottom of the reactor column below the thirteenth tray with a flow rate of about 2.9 m$^3$/hr. The reaction temperature in the reactor column was about 80° C. A reaction mixture was obtained at the bottom of the reactor column and had the following composition: about 29.16% by weight of bisphenol-A, about 69.94% by weight of phenol, about 0.686% by weight of 2,4-bisphenol-A, about 0.323% by weight of triphenol, about 0.0837% by weight of chroman, about 0.22% by weight of water and about 0.135% by weight of other materials. The reaction mixture was directly fed in a continuous manner into a primary crystallizer in which the temperature of the reaction mixture was decreased from about 80° C. to about 42° C. to obtain a crystal slurry containing adduct crystals of bisphenol-A and phenol in 1:1 molar ratio. The crystal slurry was then filtered and penetratively washed once with fresh phenol the amount of which was about one-fourth by volume of the adduct crystals, to obtain adduct crystals. The majority of adduct crystals had a particle size of about 210 μm, variation coefficient of about 37% and crystal purity of about 99.90%.

The adduct crystals were heated to about 130° C. and melted. They then were fed into a distillation column to remove at least most of the phenol. The distillation column was operated under reduced pressure of about 50 mmHg (abs.). The temperature at the top of the reactor column was about 104° C., and the temperature at the bottom of the reactor column was about 180° C. Bisphenol-A containing about 3% phenol was obtained at the bottom of the distillation column and then fed continuously into a descending film dephenolizing device the operating conditions of which were as follows: the feed temperature was about 180° C., the temperature at the bottom of the device was about 224° C. and the operation pressure in the device system was about 5 mmHg (abs.). The bisphenol-A product was discharged from the descending film dephenolizing device which had a purity of about 99.9% by weight; a free phenol content of about 20 ppm and color of about 10 APHA (in 50% ethanol). This product had the quality sufficient to meet the need for high purity bisphenol-A when it is desired to manufacture high quality bisphenol-A. In order to obtain an ultrapure bisphenol-A product, about 258 g of the above high purity or polycarbonate grade bisphenol-A crystals were fed into a solvent recrystallizer which was operated by using a mixture of toluene and water as a solvent. The solvent mixture contained about 602 g toluene and about 80.6 g water. The temperature was lowered from about 85° C. to about 35° C. The operation time was 3.5 hours. The bisphenol-A crystals obtained by solid-liquid separation were washed with toluene. The amount of toluene used was about 120 g and the washing temperature was about 40° C. The washed bisphenol-A product was dried under vacuum to give about 245 g of an ultrapure bisphenol-A product which had the following characteristics:

| bisphenol-A | >99.99% |
| melting point | 156.8° C. |
| free phenol | 0 |
| ash | 0.01% |
| iron ion | not determined |
| color (in 50% ethanol) | 8 APHA |

COMPARATIVE EXAMPLE 1

The condensation reaction of phenol and acetone was carried out in a fixed bed reactor column. The reactor column has a diameter of about 70 mm and height of about 4186 mm. In the reactor column, particulate catalyst beds were provided in three sections each of which has a length of about 1000 mm. To the beds was loaded the same modified strong acid ion-exchange resin catalyst as that used in the multiple stage suspended reactive stripping column. The molar ratio of phenol to acetone of the feedstock charged to the reactor column was about 8:1 and the total feed rate was about 6.05 kg/hr. The reaction temperature was about 70° C. The condensation reaction mixture discharged from the fixed bed reactor column had the following composition: about 17.96% by weight of bisphenol-A, about 81.35% by weight of phenol, about 0.373% by weight of 2,4-bisphenol-A, about 0.187% by weight of water, about 0.130% by weight of triphenol and about 0.030% by weight of chroman. The condensation reaction mixture was fed into a column for removing lower boiling components wherein a portion of phenol, water formed during the condensation reaction and acetone are removed to obtain a concentrate which had the following composition: about 30.08% by weight of bisphenol-A, about 68.11% by weight of phenol, about 0.95% by weight of 2,4-bisphenol-A, about 0.57% by weight of triphenol, about 0.12% by weight of chroman and about 0.15% by weight of others.

The concentrate was recrystallized, filtrated, washed and dephenolized as described in example 1 to obtain a bisphenol-A product which had the following characteristics:

| bisphenol-A | 99.99% |
| melting point | 156.5° C. |
| free phenol | 100 ppm |
| color (in 50% ethanol) | 20 APHA |

As can be seen from the comparative example, due to the lower concentration in the condensation reaction mixture discharged from the fixed bed reactor column, it is necessary to undergo a concentration procedure in order to remove the lower boiling components before the adduct crystals of phenol and bisphenol-A in 1:1 molar ratio is precipitated when cooled. This notonly increases the energy consumption and subjects the desired reaction product to thermal effect once more but also increase the impurity content in the concentrate. In effect, the impurity content in the concentrate is much more than that in the condensation reaction mixture from the multiple stage suspended reactor column so that the color of the finally obtained bisphenol-A product is importantly affected.

EXAMPLE 2

A condensation reaction mixture was obtained from a multiple stage suspended bed reactor column as substantially described in example 1. The reaction mixture was then directly fed into a crystallizing device at the rate of about 6 kg/hr. The temperature of the reaction mixture was lowered from about 80° C. to about 42° C. in the crystallizing device to allow the reaction mixture for primary crystallization. In order to increase the particle size of the adduct crystals and to improve the size distribution, a fine crystal destructor system as specifically described hereinabove was employed. Two cylindrical filters were provided in the primary crystallizer. The filters were covered with about 120 mesh sieve screens composed of stainless steel filaments and were connected to each other by an external circulating pump and two tube-type fine crystal destructors provided before and after the pump, respectively.

During the operation of the fine crystal destructor system, the crystal slurry containing only fine crystals of size smaller than 125 μm was pumped out by the circulating pump to pass through the pipeline of the crystal destructor. Hot water at a temperature of about 85° C. was passed through the shell side. The fine crystals were molten when heated and then returned back to the primary crystallizer through another filter equipped in the crystallizer by the circulating pump. The transportation or delivery direction of the circulating pump was reversed once every about 35 minutes and the filtration and wash functions of the two filters are altered. The adduct crystal slurry obtained from the primary crystallizer connected with the fine crystal destructor system was filtered and washed to obtain adduct crystals. The majority of the adduct crystals had a particle size of about 390 μm, variation coefficient of about 21%, and adduct crystal purity of more than about 99.99%. The adduct crystals were dephenolized as described in example 1 to obtain a bisphenol-A product which had the following characteristics:

| bisphenol-A | 99.95% |
|---|---|
| melting point | 156.8° C. |
| free phenol | 20 ppm |
| color (in 50% ethanol) | 10 APHA |

The bisphenol-A crystals thus obtained were recrystallized from toluene-water binary solvent as described in example 1 to obtain an ultrapure bisphenol-A product which had the following characteristics:

| bisphenol-A | >99.99% |
|---|---|
| melting point | 156.8° C. |
| free phenol | 0 |
| color (in 50% ethanol) | 7 APHA |

EXAMPLE 3

The adduct crystals were obtained according to the procedures as described in example 1. The adduct crystals were then subjected to solid phase dephenolization. The vacuum dephenolizing device used in this example was a commercially available vacuum oven which had been modified. More particularly, it was equipped with a vacuum system and a condensated phenol collector. Vacuum was established in the system containing adduct crystals and constantly maintained at about 10 mmHg (abs.) during the dephenolization. The operation time was about 4 hours. the temperatures were elevated from about 50° C. to about 130° C. in a programmed manner during the dephenolization operation and were controlled as follows: from about 50° C. to about 85° C. for about 60 min., from about 85° C. to about 110° C. for about 60 min. and from about 110° C. to about 130° C. for 120 min. A high purity or polycarbonate grade bisphenol-A product was obtained directly from the vacuum oven after the dephenolization. The bisphenol-A thus obtained had the following characteristics:

| bisphenol-A | 99.90% |
|---|---|
| melting point | 156.8° C. |
| free phenol | 85 ppm |
| color (in 50% ethanol) | 7 APHA |

The bisphenol-A product thus obtained was recrystallized from toluene-water binary solvent as described in example 1 to obtain an ultrapure bisphenol-A product which had the following characteristics:

| bisphenol-A | >99.99% |
|---|---|
| melting point | 156.8° C. |
| free phenol | 0 |
| color (in 50% ethanol) | 5 APHA |

EXAMPLE 4

A reaction mixture was obtained from a multiple stage suspended reactor column according to the procedures as described in example 1. The reaction mixture was then fed into the same crystallizer connected with a fine crystal destructor system as that described in example 2 and cooled to precipitate adduct crystals of bisphenol-A and phenol under the same conditions as those described in example 2.

The adduct crystal slurry thus obtained was filtered and washed and then the separated adduct crystals were fed into a vacuum dephenolizing device to remove phenol from the adduct crystals under the same dephenolizing conditions as those in example 3. The bisphenol-A product thus obtained had the following characteristics:

| bisphenol-A | 99.99% |
|---|---|
| melting point | 156.8° C. |
| free phenol | 80 ppm |
| color (in 50% ethanol) | 7 APHA |

This bisphenol-A product was recrystallized from toluene-water binary solvent as described in example 3 to obtain an ultrapure bisphenol-A product. The product thus obtained had the following characteristics:

| bisphenol-A | >99.999% |
|---|---|
| melting point | 156.8° C. |
| free phenol | 0 |
| color (in 50% ethanol) | 5 APHA |

EXAMPLE 5

About 980 g of condensation reaction mixture was obtained from a multiple stage suspended bed reactor column as described in example 1. The operation temperature of the reactor column was about 80° C. and the residence time was about 1.5 hours. The molar ratio of phenol to acetone charged to the reactor column was about 7:1. The condensation reaction mixture obtained contains about 31% by weight of bisphenol-A, about 0.58% by weight of 2, 4-bisphenol-A, about 0.42% by weight of other by-products and impurities. The reaction mixture was cooled from about 80° C. to about 42° C. to precipitate the adduct crystals of bisphenol-A and phenol in 1:1 molar ratio and 460.6 g of adduct crystals were then obtained by solid-liquid separation.

The adduct crystals thus obtained were fed into a gas-solid dephenolizing device and phenol was removed under vacuum. The operating conditions in the dephenolizing device were as follows: the absolute pressure was about 5 mmHg, the body temperature was controlled between about 60° C. and about 100° C. and the operation time was about 2.5 hours. About 258 g of high purity or polycarbonate grade bisphenol-A was obtained after dephenolization. The product had the following characteristics:

| | |
|---|---|
| purity | >99.9% |
| melting point | >156.8° C. |
| free phenol | <100 ppm |
| ash | <0.01% |
| color (in 50% ethanol) | <10 APHA |
| iron | <0.1 ppm |

EXAMPLE 6

About 258 g of high purity or polycarbonate grade bisphenol-A product was obtained according to the procedures as described in example 5. The bisphenol-A product was then fed into a solvent recrystallizer. Toluene and water were used as a solvent, i.e. about 602 g toluene and about 80.6 g water were used. The resulting mixture was cooled from about 85° C. to about 35° C. and the residence time in the recrystallizer was about 3.5 hours. Bisphenol-A obtained by solid-liquid sepatation was washed with toluene, the amount of which was about 120 g, at a washing temperature of about 40° C. Subsequently, the bisphenol-A product was dried under vacuum to give about 245 g ultrapure bisphenol-A product. The product had the following characteristics:

| | |
|---|---|
| bisphenol-A | >99.999% |
| melting point | >156.8° C. |
| free phenol | 0 |
| ash | <0.01% |
| color (in 50% ethanol) | 5 APHA |
| iron | not determined |

Industrial Applicability

The present invention may be carried out to produce quality bisphenol-A products which have high purity or polycarbonate grade purity of up to 99.9% and ultrapurity of more than 99.9%, preferably 99.99% or more and color of less than 15 APHA, preferably 10 APHA, more preferably less than 8 APHA and even 4 APHA. These bisphenol-A products may be used to manufacture a lot of polymers and other products. More particularly, these bisphenol-A products are employed to make optical discs for storage a data.

Further, the present invention is hereinbefore described fur purposes of explanation and illustration according to a particularly preferred embodiment for the production of high purity and ultrapure bisphenol-A. It will be apparent to those skilled in the art that many modifications and changes in connection with the general reactive stripping process and apparatus, fine crystal destructor means and gas-solid dephenolization process may be made within the scope and spirit of the present invention as generally defined in the following appended claims.

We claim:

1. A process for the production of bisphenol-A comprising the steps of (1) reacting excess phenol and acetone in the presence of catalyst, (2) cooling the reaction mixture to form adduct crystals of bisphenol-A with phenol and a first mother liquor, (3) separating the adduct crystals from the first mother liquor and (4) removing phenol from the adduct crystals wherein in step (1), excess phenol is reacted with acetone in a substantially vertical, multiple stage suspended reactive stripping apparatus comprising (i) a reactor column which includes a side wall and a bottom, (ii) a plurality of perforated trays provided in the reactor column, (iii) a first screen located on each tray, (iv) a plurality of downcomers interconnecting the trays, each of the downcomers having a second screen connected to the top thereof, the second screen, a portion of each said downcomers, a portion of the side wall of the reactor column and one of the perforated trays with the first screen thereon in combination defining a catalyst chamber, and (v) a modified strong acid ion-exchange resin catalyst in the form of particulate solid contained within the catalyst chamber, and wherein all of the phenol necessary for the condensation reaction thereof with acetone is charged to the reactor column from above the uppermost tray, portions of all the required acetone are charged to the tray next to the uppermost tray and at least some of the lower trays, and an inert gaseous stream is upwardly passed through the catalyst chambers to form solid-liquid suspensions and to strip water from the reaction mixture.

2. A process for the production of bisphenol-A according to claim 1 wherein in step (2), the liquid condensation reaction mixture effluent from the reactive stripping apparatus is cooled in a crystallizer to form a slurry containing crystals of the adduct of bisphenol-A and phenol and the mother liquor, said crystallizer having two filter means provided therein whereby a portion of the slurry containing fine adduct crystals of bisphenol-A and phenol having a particle size less than that of a predetermined crystalcut is allowed to pass alternatively through one of the filter means with a circulating pump and is then introduced into at least one fine crystal destructor from which a solution obtained after destruction of fine crystals is returned to the crystallizer through the other filter means with said or another circulating pump.

3. A process for the production of bisphenol-A according to claim 1 wherein step (4) comprises removing phenol from the adduct crystals obtained in step (3) by introducing the adduct crystals into at least one of a vacuum dephenolizer and an inert gaseous flow dephenolizer, bringing the adduct crystals to a temperature below the melting point thereof in the vacuum or in the presence of the inert gaseous stream to decompose the crystals into a gas phase and a solid phase, withdrawing the gas phase and discharging the solid phase as a high purity bisphenol-A product.

4. A process for the production of bisphenol-A according to claim 1 wherein the process further includes the steps of (5) recrystallizing the high purity bisphenol-A crystals obtained in step (4) above in the presence of solvent in a recrystallizer, and (6) separating the recrystallized bisphenol-A from a second mother liquor to obtain an ultrapure bisphenol-A product.

5. A process for the production of bisphenol-A according to claim 1 wherein the column trays include at least one of sieve trays and float valve trays.

6. A process for the production of bisphenol-A according to claim 1 wherein the mesh of the screen placed on the trays is smaller than the particle size of the catalyst particles.

7. A process for the production of bisphenol-A according to claim 1 wherein the catalyst load for each tray provided in the reactor column is in the range of from about 3% to about 10% by volume of the total volume of the catalyst and the reaction mixture.

8. A process for the production of bisphenol-A according to claim 1 wherein the molar ratio of phenol to acetone which is fed to the reactive stripping apparatus is in the range of from about 4 to about 12.

9. A process for the production of bisphenol-A according to claim 1 wherein the molar ratio of phenol to acetone which is fed to the reactive stripping apparatus is in the range of from about 7 to about 12.

10. A process for the production of bisphenol-A according to claim 1 wherein the molar ratio of phenol to acetone which is fed to the reactive stripping apparatus is about 7.

11. A process for the production of bisphenol-A according to claim 1 wherein the reaction temperature is in the range of from about 60° C. to about 130° C.

12. A process for the production of bisphenol-A according to claim 1 wherein the reaction temperature is in the range of from about 80° C. to about 100° C.

13. A process for the production of bisphenol-A according to claim 1 wherein the residence time calculated on the basis of dry catalyst weight is in the range of from about 0.25 to about 2 hrs.

14. A process for the production of bisphenol-A according to claim 1 wherein the inert gaseous stream comprises nitrogen.

15. A process for the production of bisphenol-A according to claim 1 wherein the velocity of the inert gaseous stream is in the range of from about 0.006 to about 0.075 m/s.

16. A process for the production of bisphenol-A according to claim 1 wherein the inert gaseous stream is removed from the reactive stripping apparatus, water is separated from the inert gaseous stream and the dewatered inert gaseous stream is then recycled to the bottom of the reactor column.

17. A process for the production of bisphenol-A according to claim 1 wherein the condensation reaction mixture effluent from step (1) is directly cooled to precipitate bisphenol-A in the form of adduct crystals containing bisphenol-A and phenol in a 1:1 molar ratio.

18. A process for the production of bisphenol-A according to claim 1 wherein the reaction mixture is cooled to more than about 40° C. in step (2).

19. A process for the production of bisphenol-A according to claim 1 wherein the reaction mixture is cooled to about 42° C. in step (2).

20. A process for the production of bisphenol-A according to claim 2 wherein phenol and acetone are fed to the reactive stripping apparatus in a phenol:acetone molar ratio of from about 4:1 to about 12:1, reaction takes place at a temperature in the range of from about 60° C. to about 130° C., and step (4) includes introducing the adduct crystals to a vacuum or inert gaseous flow dephenolizer, bringing the adduct crystals to a temperature below the melting point to decompose the crystals into a gas phase and a solid phase, and discharging the solid phase as a high purity bisphenol-A product.

21. A process for the production of bisphenol-A according to claim 20 wherein the process further includes the steps of:

(5) recrystallizing the high purity bisphenol-A obtained in step (4) in the presence of a solvent, and (6) separating the recrystallized bisphenol-A from a second mother liquor to obtain an ultrapure bisphenol-A product.

22. A process for the production of bisphenol-A, comprising:

reacting acetone and phenol to form a reaction mixture containing bisphenol-A and water, cooling the reaction mixture to form bisphenol-A-phenol adduct crystals and a mother liquor, separating the adduct crystals from the mother liquor and removing phenol from the adduct crystals to obtain bisphenol-A, wherein the reaction of acetone and phenol is conducted in a reactor column having a plurality of perforated trays supporting a solid particulate catalyst, and an inert gas is passed upwardly through the reactor column during reaction in order to agitate the catalyst particles while stripping water from the reaction mixture, thereby forming a reaction mixture effluent having a reduced water content.

23. A process for the production of bisphenol-A according to claim 22 wherein during the cooling step, the reaction mixture effluent is cooled in a crystallizer containing at least first and second filter means, a portion of the crystallized reaction mixture which has a particle size less than that of a predetermined crystalcut is pumped through the first filter means and is then introduced into a crystal destructor to obtain a dissolved solution which is then returned to the crystallizer through the second filter means, the direction of circulation through the filter means being reversed after a predetermined period of time in order that a portion of the crystallized reaction mixture is pumped through the second filter means before being introduced into the crystal destructor and is returned to the crystallizer through the first filter means.

24. A process for the production of bisphenol-A according to claim 22 wherein phenol is removed from the adduct crystals in at least one of a vacuum dephenolizer and a pneumatic dephenolizer having an inert gas flow.

25. A process for the production of bisphenol-A according to claim 23 wherein phenol is removed from the adduct crystals in at least one of a vacuum dephenolizer and a pneumatic dephenolizer having an inert gas flow.

* * * * *